(12) United States Patent
Zamierowski

(10) Patent No.: US 8,123,781 B2
(45) Date of Patent: Feb. 28, 2012

(54) SCREEN DEVICES AND METHODS FOR CLOSING TISSUE SEPARATIONS

(75) Inventor: David S Zamierowski, Overland Park, KS (US)

(73) Assignee: KCI Licensing, Inc., San Antonio, TX (US)

( * ) Notice: Subject to any disclaimer, the term of this patent is extended or adjusted under 35 U.S.C. 154(b) by 943 days.

(21) Appl. No.: 12/130,516

(22) Filed: May 30, 2008

(65) Prior Publication Data
US 2008/0228221 A1  Sep. 18, 2008

Related U.S. Application Data

(63) Continuation of application No. 10/224,852, filed on Aug. 21, 2002, now Pat. No. 7,381,211, and a continuation-in-part of application No. 11/103,056, filed on Apr. 11, 2005, now Pat. No. 7,410,495, and a continuation-in-part of application No. 11/103,052, filed on Apr. 11, 2005, now Pat. No. 7,413,571, and a continuation-in-part of application No. 11/103,403, filed on Apr. 11, 2005, now abandoned, and a continuation-in-part of application No. 11/103,022, filed on Apr. 11, 2005, now Pat. No. 7,413,570.

(51) Int. Cl.
*A61B 17/08* (2006.01)
(52) U.S. Cl. ............ 606/216; 606/151; 606/221; 602/43
(58) Field of Classification Search .................. 606/151, 606/213–217, 221, 228; 602/41–43, 58
See application file for complete search history.

(56) References Cited

U.S. PATENT DOCUMENTS 221,427 A  11/1879  Sherman
(Continued)

FOREIGN PATENT DOCUMENTS
AU  550575 A1  8/1982
(Continued)

OTHER PUBLICATIONS

"All Silicone Jackson Pratt Style Flat Drain", C. Daniel Medical, Inc., retrieved from internet Mar. 15, 2007, http://www.cdanielmedical.com/flat-drain.html, 1-2.
(Continued)

*Primary Examiner* — Gary Jackson
*Assistant Examiner* — Katherine Dowe
(74) *Attorney, Agent, or Firm* — Law Office of Mark Brown, LLC; Mark E. Brown

(57) ABSTRACT

A medical closure screen device for a separation of first and second tissue portions is provided, which includes a mesh screen comprising tubular vertical risers, vertical strands with barbed filaments, and horizontal spacers connecting the risers and strands in a grid-like configuration. An optional perimeter member partly surrounds the screen and can comprise a perimeter tube fluidically coupled with the vertical risers to form a tubing assembly. Various input/output devices can optionally be connected to the perimeter tube ends for irrigating and/or draining the separation according to methodologies of the present invention. Separation closure, irrigation and drainage methodologies are disclosed utilizing various combinations of closure screens, tubing, sutures, fluid transfer elements and gradient force sources. The use of mechanical forces associated with barbed strands for repositionably securing separated tissues together is disclosed. The use of same for eliminating or reducing the formation of subcutaneous voids or pockets, which can potentially form hematoma and seroma effects, is also disclosed.

5 Claims, 31 Drawing Sheets

U.S. PATENT DOCUMENTS

| | | |
|---|---|---|
| 1,355,846 A | 10/1920 | Rannells |
| 2,547,758 A | 4/1951 | Keeling |
| 2,632,443 A | 3/1953 | Lesher |
| 2,682,873 A | 7/1954 | Evans et al. |
| 2,969,057 A | 1/1961 | Simmons |
| 3,066,672 A | 12/1962 | Crosby, Jr. |
| 3,115,138 A | 12/1963 | McEvenny et al. |
| 3,367,332 A | 2/1968 | Groves |
| 3,520,300 A | 7/1970 | Flower |
| 3,648,692 A | 3/1972 | Wheeler |
| 3,682,180 A | 8/1972 | McFarlane |
| 3,826,254 A | 7/1974 | Mellor |
| 3,981,051 A | 9/1976 | Brumlik |
| 4,080,970 A | 3/1978 | Miller |
| 4,096,853 A | 6/1978 | Weigand |
| 4,139,004 A | 2/1979 | Gonzalez |
| 4,165,748 A | 8/1979 | Johnson |
| 4,233,969 A | 11/1980 | Lock et al. |
| 4,245,630 A | 1/1981 | Lloyd et al. |
| 4,248,232 A | 2/1981 | Engelbrecht et al. |
| 4,259,959 A | 4/1981 | Walker |
| 4,261,363 A | 4/1981 | Russo |
| 4,275,721 A | 6/1981 | Olson |
| 4,284,079 A | 8/1981 | Adair |
| 4,297,995 A | 11/1981 | Golub |
| 4,333,468 A | 6/1982 | Geist |
| 4,373,519 A | 2/1983 | Errade et al. |
| 4,392,853 A | 7/1983 | Muto |
| 4,392,858 A | 7/1983 | George et al. |
| 4,398,910 A * | 8/1983 | Blake et al. .................. 604/266 |
| 4,419,093 A | 12/1983 | Deaton |
| 4,419,097 A | 12/1983 | Rowland |
| 4,452,245 A * | 6/1984 | Usher ........................... 606/151 |
| 4,475,909 A | 10/1984 | Eisenburg |
| 4,480,638 A | 11/1984 | Schmid |
| 4,525,166 A | 6/1985 | Leclerc |
| 4,525,374 A | 6/1985 | Vailancourt |
| 4,540,412 A | 9/1985 | Van Overloop |
| 4,543,100 A | 9/1985 | Brodsky |
| 4,548,202 A | 10/1985 | Duncan |
| 4,551,139 A | 11/1985 | Plaas et al. |
| 4,569,348 A | 2/1986 | Hasslinger |
| 4,605,399 A | 8/1986 | Weston et al. |
| 4,608,041 A | 8/1986 | Nielson |
| 4,640,688 A | 2/1987 | Hauser |
| 4,655,754 A | 4/1987 | Richmond et al. |
| 4,696,301 A | 9/1987 | Barabe |
| 4,710,165 A | 12/1987 | McNeil et al. |
| 4,733,659 A | 3/1988 | Edenbank et al. |
| 4,743,232 A | 5/1988 | Kruger |
| 4,758,220 A | 7/1988 | Sundblom et al. |
| 4,787,888 A | 11/1988 | Fox |
| 4,826,494 A | 5/1989 | Richmond et al. |
| 4,828,546 A | 5/1989 | McNeil et al. |
| 4,838,883 A | 6/1989 | Matsuura |
| 4,840,187 A | 6/1989 | Brazier |
| 4,863,449 A | 9/1989 | Therriault et al. |
| 4,872,450 A | 10/1989 | Austad |
| 4,878,901 A | 11/1989 | Sachse |
| 4,897,081 A | 1/1990 | Poirier et al. |
| 4,906,233 A | 3/1990 | Moriuchi et al. |
| 4,906,240 A | 3/1990 | Reed et al. |
| 4,919,654 A | 4/1990 | Kait |
| 4,941,882 A | 7/1990 | Ward et al. |
| 4,953,565 A | 9/1990 | Tachibana et al. |
| 4,969,880 A | 11/1990 | Zamierowski |
| 4,976,726 A | 12/1990 | Haverstock |
| 4,985,019 A | 1/1991 | Michelson |
| 5,007,921 A | 4/1991 | Brown |
| 5,007,936 A | 4/1991 | Woolson |
| 5,019,083 A | 5/1991 | Klapper et al. |
| 5,037,397 A | 8/1991 | Kalt et al. |
| 5,045,054 A | 9/1991 | Hood et al. |
| 5,086,170 A | 2/1992 | Luheshi et al. |
| 5,092,858 A | 3/1992 | Benson et al. |
| 5,100,396 A | 3/1992 | Zamierowski |
| 5,112,338 A | 5/1992 | Anspach, III |
| 5,134,994 A | 8/1992 | Say |
| 5,139,023 A | 8/1992 | Stanley et al. |
| 5,149,331 A | 9/1992 | Ferdman et al. |
| 5,167,613 A | 12/1992 | Karami et al. |
| 5,169,399 A | 12/1992 | Ryland et al. |
| 5,176,663 A | 1/1993 | Svedman et al. |
| 5,215,522 A | 6/1993 | Page et al. |
| D337,639 S | 7/1993 | Beckman |
| 5,232,453 A | 8/1993 | Plass et al. |
| 5,261,893 A | 11/1993 | Zamierowski |
| 5,278,100 A | 1/1994 | Doan et al. |
| 5,279,550 A | 1/1994 | Habib et al. |
| 5,291,887 A | 3/1994 | Stanley et al. |
| 5,298,015 A | 3/1994 | Komatsuzaki et al. |
| 5,318,570 A | 6/1994 | Hood et al. |
| 5,342,376 A | 8/1994 | Ruff |
| 5,344,415 A | 9/1994 | Debusk et al. |
| 5,358,494 A | 10/1994 | Svedman |
| 5,383,897 A | 1/1995 | Wholey |
| 5,423,885 A | 6/1995 | Williams |
| 5,437,622 A | 8/1995 | Carion |
| 5,437,651 A | 8/1995 | Todd et al. |
| 5,507,833 A | 4/1996 | Bohn |
| 5,522,901 A | 6/1996 | Thomas et al. |
| 5,527,293 A | 6/1996 | Zamierowski |
| D372,309 S | 7/1996 | Heldreth |
| 5,549,584 A | 8/1996 | Gross |
| 5,556,375 A | 9/1996 | Ewall |
| 5,580,353 A | 12/1996 | Mendes |
| 5,584,859 A | 12/1996 | Brotz |
| 5,607,388 A | 3/1997 | Ewall |
| 5,630,819 A | 5/1997 | Ashby et al. |
| 5,636,643 A | 6/1997 | Argenta et al. |
| 5,645,081 A | 7/1997 | Argenta et al. |
| 5,716,360 A | 2/1998 | Baldwin et al. |
| 5,738,686 A | 4/1998 | Kubein-Meesenburg et al. |
| 5,785,700 A | 7/1998 | Olson |
| 5,800,546 A | 9/1998 | Marik et al. |
| 5,827,246 A | 10/1998 | Bowen |
| 5,846,244 A | 12/1998 | Cripe |
| 5,911,222 A | 6/1999 | Lawrence et al. |
| 5,921,972 A | 7/1999 | Skow |
| 5,931,855 A | 8/1999 | Buncke |
| 5,941,859 A | 8/1999 | Lerman |
| 6,071,267 A | 6/2000 | Zamierowski |
| 6,113,618 A | 9/2000 | Nic |
| 6,126,659 A | 10/2000 | Wack |
| 6,135,116 A | 10/2000 | Vogel et al. |
| 6,142,982 A | 11/2000 | Hunt et al. |
| 6,146,423 A | 11/2000 | Cohen et al. |
| 6,159,246 A | 12/2000 | Mendes et al. |
| 6,174,306 B1 | 1/2001 | Fleischmann |
| 6,179,804 B1 | 1/2001 | Satterfield |
| 6,190,391 B1 | 2/2001 | Stubbs |
| 6,190,392 B1 | 2/2001 | Vandewalle |
| 6,203,563 B1 | 3/2001 | Fernandez |
| 6,241,747 B1 | 6/2001 | Ruff |
| 6,270,517 B1 | 8/2001 | Brotz |
| RE37,358 E | 9/2001 | Del Rio et al. |
| 6,287,316 B1 | 9/2001 | Agarwal et al. |
| 6,293,929 B1 | 9/2001 | Smith et al. |
| 6,345,623 B1 | 2/2002 | Heaton et al. |
| 6,355,215 B1 | 3/2002 | Poggie et al. |
| 6,377,653 B1 | 4/2002 | Lee et al. |
| 6,398,767 B1 | 6/2002 | Fleischmann |
| 6,430,427 B1 | 8/2002 | Lee et al. |
| 6,488,643 B1 | 12/2002 | Turney |
| 6,493,568 B1 | 12/2002 | Bell et al. |
| 6,500,209 B1 | 12/2002 | Kolb |
| 6,503,281 B1 | 1/2003 | Mallory |
| 6,540,705 B2 | 4/2003 | Norstream et al. |
| 6,553,998 B2 | 4/2003 | Heaton et al. |
| 6,589,285 B2 | 7/2003 | Penenberg |
| 6,620,132 B1 | 9/2003 | Skow |
| 6,626,891 B2 | 9/2003 | Ohmstede |
| 6,645,226 B1 | 11/2003 | Jacobs et al. |
| 6,669,735 B1 | 12/2003 | Pelissier |
| 6,685,681 B2 | 2/2004 | Lockwood et al. |
| 6,695,823 B1 | 2/2004 | Lina et al. |
| 6,695,824 B2 * | 2/2004 | Howard et al. .................. 604/305 |

| | | |
|---|---|---|
| 6,726,706 B2 | 4/2004 | Dominguez |
| 6,752,794 B2 | 6/2004 | Lockwood et al. |
| 6,800,074 B2 | 10/2004 | Henley et al. |
| 6,814,079 B2 | 11/2004 | Heaton et al. |
| 6,824,533 B2 | 11/2004 | Risk, Jr. et al. |
| 6,828,468 B2 | 12/2004 | Leavanoni et al. |
| 6,856,821 B2 | 2/2005 | Johnson |
| 6,860,903 B2 | 3/2005 | Mears et al. |
| 6,953,480 B2 | 10/2005 | Mears et al. |
| 6,991,643 B2 | 1/2006 | Saadat |
| 7,108,683 B2 | 9/2006 | Zamierowski |
| 7,381,211 B2 | 6/2008 | Zamierowski |
| 2002/0022861 A1 | 2/2002 | Jacobs et al. |
| 2002/0029063 A1 | 3/2002 | Wittman |
| 2002/0077661 A1 | 6/2002 | Saadat |
| 2002/0099447 A1 | 7/2002 | Mears et al. |
| 2002/0111595 A1 | 8/2002 | Haarer |
| 2002/0116067 A1 | 8/2002 | Mears et al. |
| 2002/0120185 A1 | 8/2002 | Johnson |
| 2002/0143286 A1 | 10/2002 | Turney |
| 2002/0161317 A1* | 10/2002 | Risk et al. ............. 602/2 |
| 2002/0183565 A1 | 12/2002 | Leavanoni et al. |
| 2002/0198503 A1 | 12/2002 | Risk, Jr. et al. |
| 2003/0050594 A1 | 3/2003 | Zamierowski |
| 2003/0097135 A1 | 5/2003 | Penenberg |
| 2004/0039415 A1 | 2/2004 | Zamierowski |
| 2005/0043818 A1 | 2/2005 | Bellon et al. |

FOREIGN PATENT DOCUMENTS

| | | |
|---|---|---|
| AU | 745271 | 12/2002 |
| AU | 755496 | 12/2002 |
| CA | 2005436 | 6/1990 |
| DE | 2640413 | 3/1978 |
| DE | 4306478 | 9/1994 |
| DE | 29504378 | 9/1995 |
| EP | 0100148 | 2/1984 |
| EP | 0117632 | 9/1984 |
| EP | 0161865 | 11/1985 |
| EP | 0358302 | 3/1990 |
| EP | 1018967 | 8/2004 |
| EP | 1513478 | 12/2009 |
| GB | 692578 | 6/1953 |
| GB | 2197789 | 6/1988 |
| GB | 2220357 | 1/1990 |
| GB | 2 235 877 | 3/1991 |
| GB | 2235877 | 3/1991 |
| GB | 2333965 | 8/1999 |
| GB | 2329127 | 8/2000 |
| JP | 4129536 | 4/1992 |
| SG | 71559 | 4/2002 |
| WO | WO-80/02182 | 10/1980 |
| WO | WO93/09727 | 5/1993 |
| WO | WO94/20041 | 9/1994 |
| WO | WO96/05873 | 2/1996 |
| WO | WO97/18007 | 5/1997 |
| WO | WO99/13793 | 9/1998 |

OTHER PUBLICATIONS

"All Silicone Jackson Pratt Style Round Drain", C. Daniel Medical, Inc., retrieved from internet Mar. 15, 2007, http://www.cdanielmedical.com/round-drain.html, 1-2.

Jeschke, Marc G., et al., "Development of New Reconstructive Techniques: Use of Integra in Combination with Fibrin Glue and Negative-Pressure Therapy fro Reconstruction of Acute and Chronic Wounds", Departments of General Surgery and Trauma and Reconstructive Surgery, University of Regensburg, (Jan. 15, 2003), 525-530.

Svedman, Pal et al., "A Dressing System Providing Fluid Supply and Suction Drainage Used for Continuous or Intermittent Irrigation", Annals of Plastic Surgery, vol. 17, No. 2, (Aug. 1986), 125-133.

Svedman, Pal "A Dressing Allowing Continuous Treatment of a Biosurface", IRCS Medical Science: Biomedical Technology; Clinical Medicine; Surgery and Transplantation, (Jul. 1979), 221.

Arnljots, Bjorn et al., "Irrigation Treatment in Split-Thickness Skin Grafting of Intractable Leg Ulcers", Scand J. Plast. Reconstr. Surg., 19, (Nov. 19, 1984),211-213.

Chinn, Steven D., et al., "Closed Wound Suction Drainage", The Journal of Foot Surgery, vol. 1, No. 1, (1985).

Svedman, Pal "Irrigation Treatment of Leg Ulcers", The Lancet, vol. 322, Issue 8349, (Sep. 3, 1983), 532-534.

Egnell, Einar "Pump AB", Industrigation2, 461, 37 Trollhattan, (Feb. 3, 1983).

Egnell, Einar "Egnell Minor Instruction Book, 1st Edition, 300 7502", (Feb. 1975),1-24.

Chariker, Mark E., et al., "Effective Management of Incisional and Cutaneous Fistulae with Closed Suction Wound Drainage", Contemporary Surgery, vol. 34, (Jun. 1989),59-63.

Venturi, Mark L., et al., "Mechanisms and CLinical Applications of the Vacuum-Assisted Closure (VAC) Device", Am. J. Clin. Dermatol., vol. 6 (3), (2005), 185-194.

"Specific Dressing Techniques and Specialty Dressings", 25.

"V.A.C. Therapy Clinical Guidelines", KCI The Clinical Advantage, www.woundvac.com, (2007).

Ambrosio, Archel et al., "V.A.C. GranuFoam Silver Dressing A New Antimicrobial Silver Foam Dressing Specifically Engineered for Use with V.A.C. Therapy", http://silverlon.com/fda.html, retrieved from the internet Jul. 27, 2006, 1-71.

Kuznetsov, V A., et al., "Vacuum and Vacuum-Sorption Treatment of open Septic Wounds, Appendix B", II All-Union Conference on Wounds and Wound Infections: Presentation Abstracts Moscow, U.S.S.R., (Oct. 29, 1986), 91-92.

Mendez-Eastman, Susan "When Wounds Won't Heal", RN, (Jan. 1998),20-24.

Bagautdinov, N. A., "Variant of External Aspiration in the Treatment of Purulent Diseases of Soft Tissues", Ministry of Higher and Secondary Education of the RSFSR I.N Ulyanov Chuvash State University, Variant of External Aspiration in the Treatment of Purulent Diseases of Soft Tissues, 94-96.

Herte, Mary C., et al., "Comparative Wound Healing in Animal Subjects Using the Cuba System VS Conventional Surgical instruments", The American Society of Plastic and Reconstructive Surgeons, (Nov. 1978),1-19.

Antibacterial Silver Wound Dressing, Bandage, Gauze and Adhesive Strips: Silverlon Woundcare Products; retrieved from internet Jul. 27, 2006 http://www.silverlon.com/wound.htm, 1-5.

Walsh, Jennifer F., et al., "Directional Neurite Outgrowth Is Enhanced by Engineered Meningeal Cell-Coated Substrates", Tissue Engineering, vol. 11, No. 7/8, Mary Ann Liebert, Inc., (2005), 1085-1095.

Tan, S. D., et al., "Inhibition of Osteocyte Apoptosis by Fluid Flow is Mediated by Nitric Oxide", Biochemical and Biophysical Research Communications, vol. 369, Issue 4, (May 16, 2008),1150-1154.

Tan, S. D., et al., "Osteocytes Subjected to Fluid Flow Inhibit Osteoclast Formation and Bone Resorption", Bone, vol. 4, (Jul. 27, 2007), 745-751.

Takahashi, Kazutoshi et al., "Induction of Pluripotent Stem Cells from Mouse Embryonic and Adult Fibroblast Cultures by Defined Factors", Cell, vol. 126, (Aug. 25, 2006), 663-676.

Shimko, Daniel A., et al., "Effect of Porosity on the Fluid Flow Characteristics and Mechanical Properties of Tantalum Scaffolds", Journal of Biomedical Materials Research, Part B, Applied Biomaterials, (Sep. 24, 2004), 315-324.

Segvich, Sharon et al., "Uniform Deposition of Protein Incorporated Mineral Layer on Three-Dimensional Porous Polymer Scaffolds", Journal of Biomedical Materials Research Part B: Applied Biomaterials 84B(2): <http://hdl.handle.net/2027.42/57926>, (May 8, 2007),340-349.

Sachlos, E. et al., "Making Tissue Engineering Scaffolds Work. Review on the Application of Solid Freeform Fabrication Technology to the Production of Tissue Engineering Scaffolds", European Cells and Materials, vol. 5 (2003), 29-40.

Pfister, Bryan J., et al., "Neural Engineering to Produce In Vitro Nerve Constructs and Neurointerface", Neurosurgery: www.neurosurgery-online.com, (2007), 137-142.

Kwan, Michael K., et al., "A Structural Model to Describe the Nonlinear stress-Strain Behavior for Parellel-Fibered Collagenous Tissues", Journal of Biomechanical Engineering, vol. 111, (Nov. 1989), 361-363.

Wilkes, R. et al., "3D Strain Measurement in Soft Tissue: Demonstration of a Novel Inverse Finite Element Model Algorithm on MicroCT Images of a Tissue Phantom Exposed to Negative Pressure Wound Therapy", *Journal of the Mechanical Behavior of Biomedical Materials*, (Nov. 5, 2008),1-16.

Timmenga, T. T., et al., "The Effect of Mechanical Stress on Healing Skin Wounds: An Experimental Study of Rabbits Using Tissue Expansion", *British Journal of Plastic Surgery*, vol. 44, (1991), 514-519.

Solovev, Vyacheslav A., "Treatment and Prevention of Suture Failures After Gastric Resection", *S.M. Kirov Gorky State Medical Institute*, (1988),1-55.

Solovev, V. A., et al., "The Method of Treatment of Immature External Fistulas in the Upper Gastrointestinal Tract", *S.M. Kirov Gorky State Medical Institute*, (1987),1-20.

Pailler-Mattei, C. et al., "Study of Adhesion Forces and Mechanical Properties of Human Skin in vivo", *J. Adhesion Sci. Technol.*, vol. 18, No. 15-16, (2004),1739-1758.

Robledo-Ogazon, Felipe et al., "Using the Vacuum Assisted Closure System VAC in the Treatment of Infected Surgical Wounds. Clinical Experience", *Madigraphic Artemisa*, vol. 74, No. 2, (Mar.-Apr. 2006), 107-113.

Laskin, Richard S., "Minimally Invasive Total Knee Replacement Using a Mini-Mid Vastus Incision Technique and Results", *Surgical Technology Internatinal*, vol. 13, (2004), 231-238.

Khatyr, Fouad "Model of the Viscoelastic Behaviour of Skin in vivo and Study of Anisotropy", *Skin Research and Technology*, vol. 10, (2004),96-103.

Diridollou, S. et al., "In vivo Model of the Mechanical Properties of the Human Skin Under Suction", *Skin Research and Technology*, vol. 6, (2000),214-221.

Delalleau, Alexandre et al., "Characterization of the Mechanical Properties of Skin by Inverse Analysis Combined with the Indentation Test", *Journal of Biomechanics*, vol. 39 (2006),1603-1610.

Dee, A. "The Successful MLanagement of a dehisced Surgical Wound with TNP Following Femoropopliteal Bypass", *Journal of Wound Care*, vol. 16, No. 1, (Jan. 2007), 42-44.

Cunningham, Kim "Development of in-vitro Model to Simulate Dermal Wound Bed Interaction with Granufoam and Gauze Dressing Under Sub Atmospheric Pressure", *Micro CT Study-Test Cell Development, Report*, (Jul. 30, 2006),1-19.

Boersma, Saskia M., et al., "Photogrammetric Wound Measurement with a Three-Camera Vision System", *IAPRS*, vol. 33, (2000).

Norman, James J., et al., "Methods for Fabrication of Nanoscale Topography for Tissue Engineering Scaffolds", *Annals of Biomedical Engineering*, vol. 34, No. 1, (Jan. 2006), 89-101.

Mikos, Antonios G., et al., "Preparation of Poly(glycolic acid) Bonded Fiber Structures for Cell Attachment and Transplantation", *Journal of Biomedical Materials Research*, vol. 27, (1993), 183-189.

Mercier, Nichole R., et al., "Poly(lactide-co-glycolide) microspheres as a moldable scaffold for Cartilage Tissure Engineering", *Biomaterials*, vol. 26 (2005),1945-1952.

Manwaring, Michael E., et al., "Contact Guidance Induced Organization of Extracellular Matrix", *Biomaterials*, vol. 25, (2004), 3631-3638.

Manwaring, Michael E., et al., "Characterization of Rat Meningeal Cultures on Materials of Differing Surface Chemistry", *Biomaterials*, vol. 22, (2001).

Lago, Natalia et al., "Neurobiological Assessment of Regenerative Electrodes for Bidirectional Interfacing Injured Peripheral Nerves", *IEEE Transactions on Biomedical Engineering*, vol. 54, No. 6, (Jun. 2007),1129-1137.

"NPD 1000 Negative Pressure Wound Therapy System", *Kalypto Medical*: www.kalyptomedical.com, (Sep. 2008),1-4.

Gemmiti, B. S., et al., "Fluid Glow Increases Type II Collagen Deposition and Tensile Mechanical Properties in Bioreactor-Grown Tissue-Engineered Cartilage", *Tissue Engineering*, vol. 12, No. 3, (2006), 469-479.

Brody, Sarah et al., "Approaches to Heart Valve Tissue Engineering Scaffold Design", *Journal of Biomedical Materials Research Part B: Applied Biomaterials*, (2006),16-43.

Anderson, Eric J., et al., "Design of Tissue Engineering Scaffolds as Delivery Devices for Mechanical and Mechanically Modulated Signals", *Tissue Engineering*, vol. 13, No. 10, (2007), 2525-2539.

Meyer, Willy et al., "Bier's Hyperemic Treatment", *W.B. Sunders Co.*, 2 Ed., (1909),1-48.

Tennant, C. E., "The Use of Hyperemia in the Postoperative Treatment of Lesions of the Extremities and Thorax", *Jour. A.M.A.*, (May 8, 1915),1548-1549.

Morykwas, Michael J., et al., "Vacuum-Assisted Closure: A new Method for Wound Control and Treatment: Animal Studies and Basic Foundation", *Annals of Plastic Surgery*, vol. 38, No. 6, (1997), 553-562.

Tribble, David E., "An Improved Sump Drain-Irrigation Device of Simple Construction", *Arch. Surg.*, vol. 105, (Sep. 1972),511-513.

Schein, M. et al., "The 'sandwich technique' Management of the Open Abdomen", *Br. J. Surg.*, vol. 73, (May 1986), 369-370.

Safronov, A. A., "Vacuum Therapy of Trophic Ulcers of the Lower Leg with Simultaneous Autoplasty of the Skin", *Ministry of Public Health of the USSR*, (1967),1-50.

Johnson, Frank E., "An Improved Technique for Skin Graft Placement Using a Suction Drain", *Surgery Gynecology & Obstetrics*, (Dec. 1984),585-586.

Zivadinovic, Gorica et al., "Vacuum THerapy in the Treatment of Peripheral Blood Vessels", *Conference Papers of the 5th Timok Medical Days, Majdanpek*, (1986).

Kaplan, Mark et al., "Guidelines for the Management of the Open Abdomen", *Supplement to Wounds*, (Oct. 2005),1-26.

Barker, Donald E., et al., "Vacuum Pack Technique of Temporary Abdominal Closure: A 7-Year Experience with 112 Patients", *The Journal Trauma: Injury, Infection and Critical Care*, vol. 48, No. 2, (Feb. 2000),201-207.

Puyana, "Resuscitation of Hypovolemic", *Textbook of Critical Care*, 5th Ed., Ch. 229, (2005),1933-1943.

Burdette, Steven D., et al., "Systemic Inflammatory Response Syndrome", eMedicine Critical Care; http://emedicine.medscape.com/article/168943-print, (Apr. 16, 2007),1-19.

Sherck, John et al., "Covering the "Open Abdomen": A Better Technique", *The American Surgeon*, vol. 64, (Sep. 1998).

Reckard, Justin M., et al., "Management of Intraabdominal Hypertension by Percutaneous Catheter Drainage", *JVIR*, vol. 16, No. 7, (Jul. 2005),1019-1021.

Gupta, Subhas et al., "Guidelines for Managing Pressure Ulcers with Negative Pressure Wound Therapy", *Supplement to Advances in Skin and Wound Care*, vol. 17, Supp. 2, (Nov. 2004),1-16.

*Merriam Webster Online Dictionary*; http: www.merriam-webster.com/dictionary/occlude_http: www.merriam-webster.com/dictionary/occlusion_retrieved from internet_Mar. 4, 2008.

Culliford, Alfred T., et al., "A Novel Technique for Vacuum Assisted Closure Device Application in Noncontiguous Wounds", *Journal of Plastic, Reconstructive and Aesthetic Surgery*, (2006),1-2.

Armstrong, David G., et al., "Planter Pressure Changes Using a Novel Negative Pressure Wound Therapy Technique", *Journal of the Am. Podiatric Med. Assoc.*, vol. 94, No. 5, (Sep. 2004), 456-460.

Poritz, Lisa S., et al., "Percutaneous Drainge and Ileocolectomy for Spontaneus Intraabdominal Abscess in Chrohn's Disease", *J. Gast. Surg.*, vol. 11, (Jan. 19, 2007), 204-207.

Garner, Glen et al., "Vacuum-Assisted Wound Closure Provides Early Fascial Reapproximation in Trauma Patients with Open Abdomens", *The Am. Journ. Surg*, vol. 182, (2001), 630-638.

Dubick, Michael A., et al., "Issues of Concern Regarding the Use of Hypertonic/Hyperoncotic Fluid Resuscitation of Hemorrahagic Hypotension", *Shock*, vol. 25, No. 4, (2006), 321-328.

Brabmamdam, Pavan et al., "Critical Care I", *Surg. Forum Abstracts*, vol. 207, No. 3S, (Sep. 2008),S34-S35.

Brock, Bradford et al., "Temporary Closure of Open Abdominal Wounds: The Vacuum Pack", *The Am. Surgeon.*, vol. 61, No. 1,(Jan. 1995), 30-35.

Baig, M. K., et al., "Percutaneous Postoperative Intra-Abdominal Abscess Drainage After Elective Colorectal Surgery", *Tech Coloproctol*, vol. 6, (2002),159-164.

"Algorithm for Abdominal Wall Construction", *Plastic and Reconstructive Surgery*, (Jan. 2000), 207-209.

Meyer, P. et al., "A New Abdominal Drain for Overflowing Lavage in Instances of Severe Pancreatitis with Persistent Peritonel Contamination", *Surgery,Gyneology & Obstetrics*, vol. 165, (Sep. 1987).

Arcand, N. et al., "Negative Pressure Wound Therapy and Its Application to Orthopaedics. Part II: Clinical Application", *Osteo Trauma Care*, (2006),254-258.

Lavery, Lawrence A., et al., "Emerging Concepts with VAC Therapy", *Podiatry Today*, vol. 20, (Jul. 1, 2007),1-6.

Latenser, Barbara A., et al., "A Pilot Study Comparing Percutaneous Decompression with Decompressive Laparotomy for Acute Abdominal Compartment Syndrome in Thermal Injury", *Journal of Burn Care & Rehab.*, vol. 23, No. 3, (May/Jun. 2002), 190-195.

"Hydrophobic Rigid Cannisters", http://www.bemishealthcare.com/docs/anisterHydrophobic, 1-1.

Aktiengesellschaft, Paul H., "Opposition to EP1513478", (Sep. 16, 2010).

Jeter, Katherine F., et al., "Managing Draining Wounds and Fistulae: New and Established Methods", *Chronic Wound Care: Health Management Publications*, (1990), 240-246.

Smith & Nephew, Inc. *Opposition against EP 1,513,478*, (Sep. 16, 2010).

"Patenee's Observations on the Oppositions", *KCI Licensing, Inc. Response to Opponents Smith & Nephew, Inc., and Paul Hartmann Aktiengesellschaft Oppositions*, EP 1513478 Wound Therapy and Tissue Treatment Management System and Method with Fluid Differentiation,(Apr. 21, 2011),1-15.

Miyauchi, Takayuki et al., "Repair of Incisional Hernia with Prolene Hernia System", *The Journal of Medical Investigation*, vol. 50, p. 108-111, 2003; received for publication Aug. 8, 2002.

Argenta, Louis C., et al., "Vacuum-Assisted Clousre: A New Method for Wound Control and Treatment: Clinical Experience", *Annals of Plastic Surgery*, vol. 38, No. 6, Jun. 1997, 563-576.

Mendez-Eastman, RN, Susan "When Wounds Won't Heal", *RN*, Jan. 1998, vol. 61(1), *Medical Economics Company, Inc.*, Montvale, NJ, USA, 20-24.

Blackburn, II, MD, James H., "Negative-Pressure Dressings as a bolster for Skin Grafts", *Annals of Plastic Surgery*, vol. 40, No. 5, May 1998, 453-457.

Masters, John "Letter to the Editor", *British Journal of Plastic Surgery*, vol. 51(3), 1998; Elsevier Science/*The British Association of Plastic Surgeons*, UK, 267.

Greer, S. E., et al., "The Use of Subatmospheric Pressure Dressing Therapy to Close Lymphocutaneous Fistulas of the Groin", *British Journal of Plastic Surgery* (2000), 53, Article No. BJPS2000, 3360,484-487.

Letsou, M.D., George V., et al., "Stimulation of Adenylate Cyclase Activity in Cultured Endothelial Cells Subjected to Cyclic Stretch", *Journal of Cardiovascular Surgery*, 31, 1980, 534-539.

"PCT/GB98/02713", *PCT International Search Report*, Jun. 8, 1999.

PCT/GB98/02713 International Applicaiton, *PCT Written Opinion*, Jun. 1999.

"PCT/GB96/02802", *PCT International Examination and Search Report*; Jan. 15, 1998 and Apr. 29, 1997.

"PCT/GB96/028202 International Application", *PCT Written Opinion*, Sep. 3, 1997.

Kostyuchenok, B. M., et al., "Vacuum Treatment in the Surgical Management of Purulent Wounds", *Vestnik Khirugi*, Sep. 1986, 18-21.

Davydov, Yu A., et al., "Vacuum Therapy in the Treatment of Purulent Lactation Mastitis", *Vestnik Khirurgi*, Sep. 1986, 66-70.

Yusupov, Yu N., et al., "Active Wound Drainage", Vestnik Khirurgi, vol. 138, Issue 4, 1987.

Davydov, Yu A., et al., "Bacteriological and Cytological Assessment of Vacuum Therapy of Purulent Wounds", *Vestnik Khirurgi*, Oct. 1998, 48-52.

Davydov, Yu A., et al., "Concepts for the Clinical-Biological Management of the Wound Process in the Treatment of Purulen: Wounds by Means of Vacuum Therapy", Vestnik Khirurgi, 1991, 132-136.

Orringer, Jay et al., "Management of Wounds in Patients with Complex Enterocutaneous Fistulas", *Surgery, Gynecology & Obstertics*, vol. 165, Jul. 1987. 79-80.

"PCT/GB95/01983", *International Search Report*, Nov. 23, 1995.

Dattilo, Jr., Philip P., et al., "Medical Textiles: Application of an Absorbable Barbed Bi-directional Surgical Suture", *Journal of Textile and Apparel, Technology and Management*, vol. 2, Issue 2, Spring 2002, 1-5.

"Search Report and Written Opinion of the International Search Authority", International Applicaiton No. PCT/US06/38855 filed Oct. 3, 2006, report issued Aug. 8, 2007.

* cited by examiner

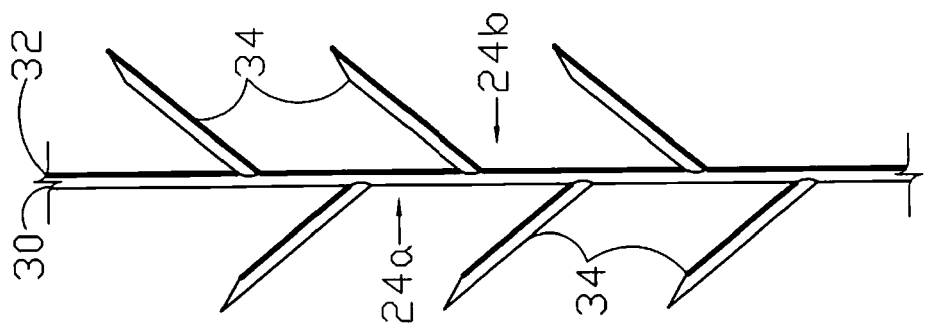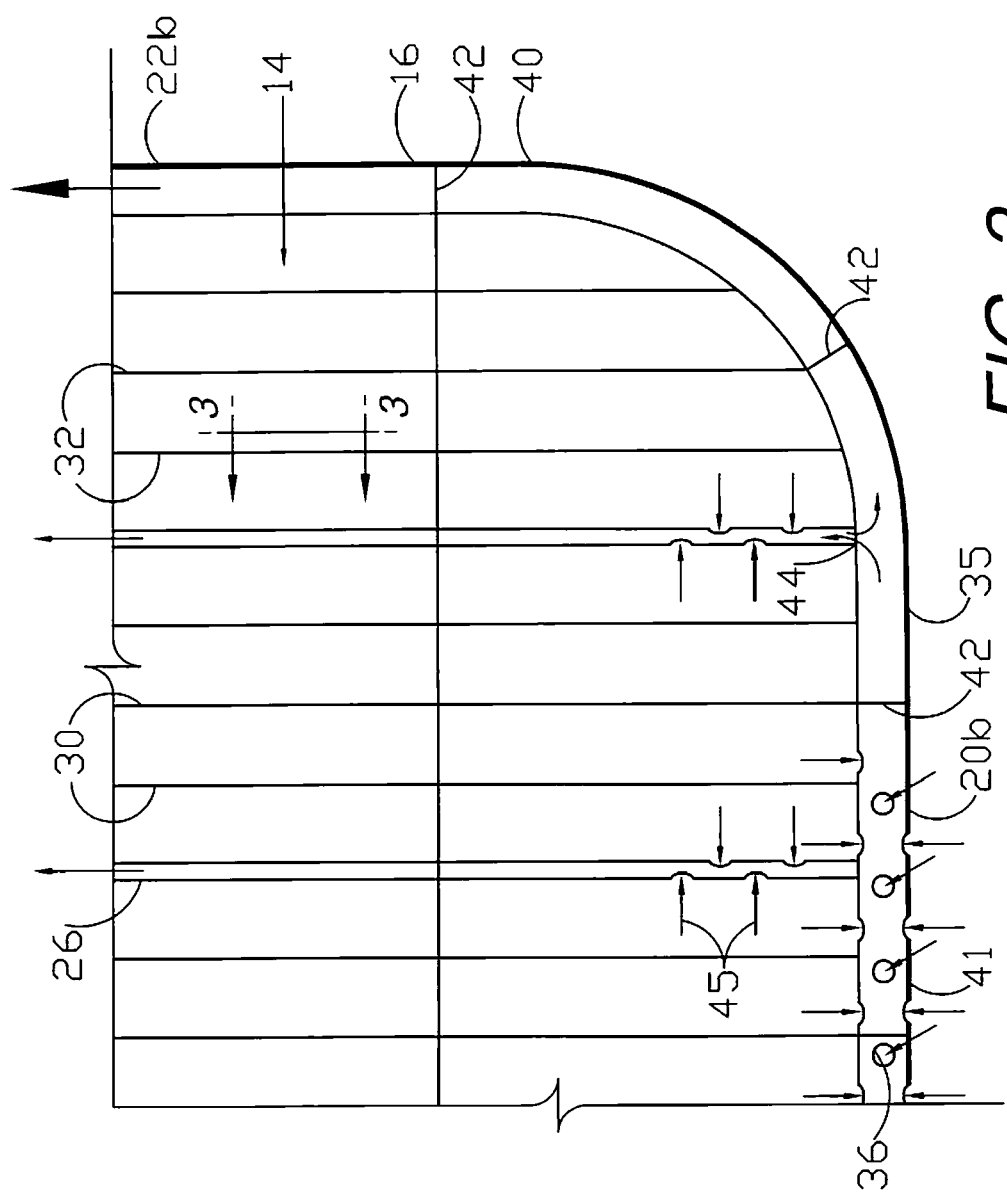

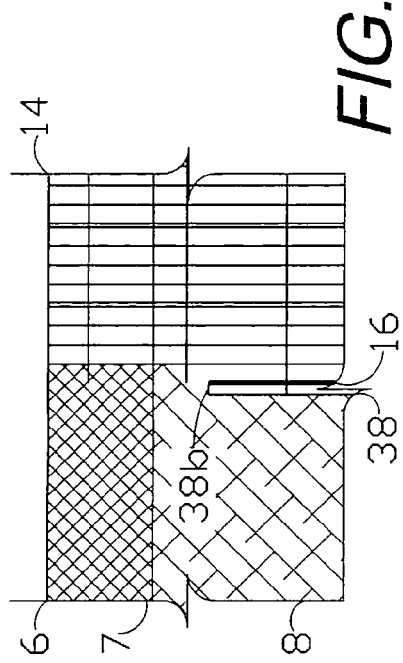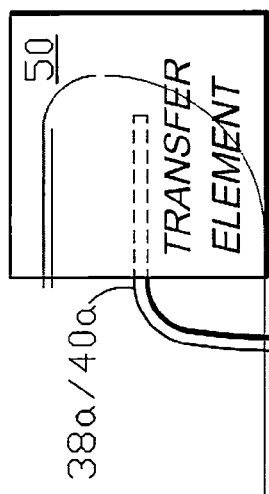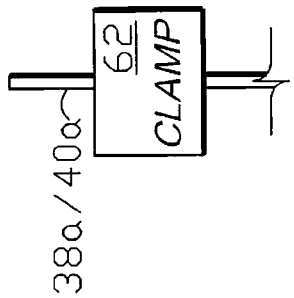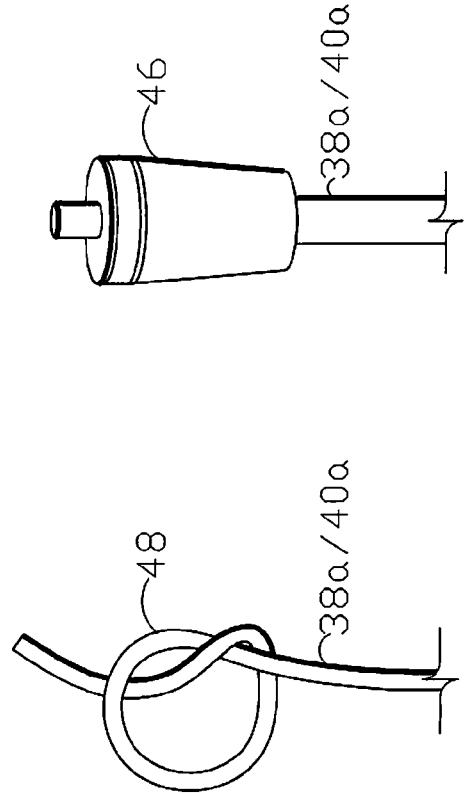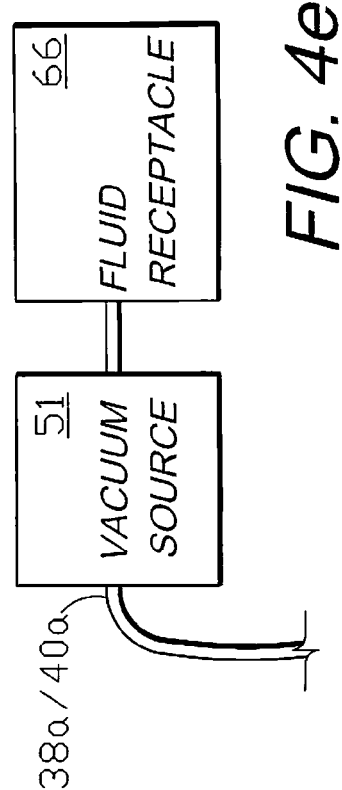

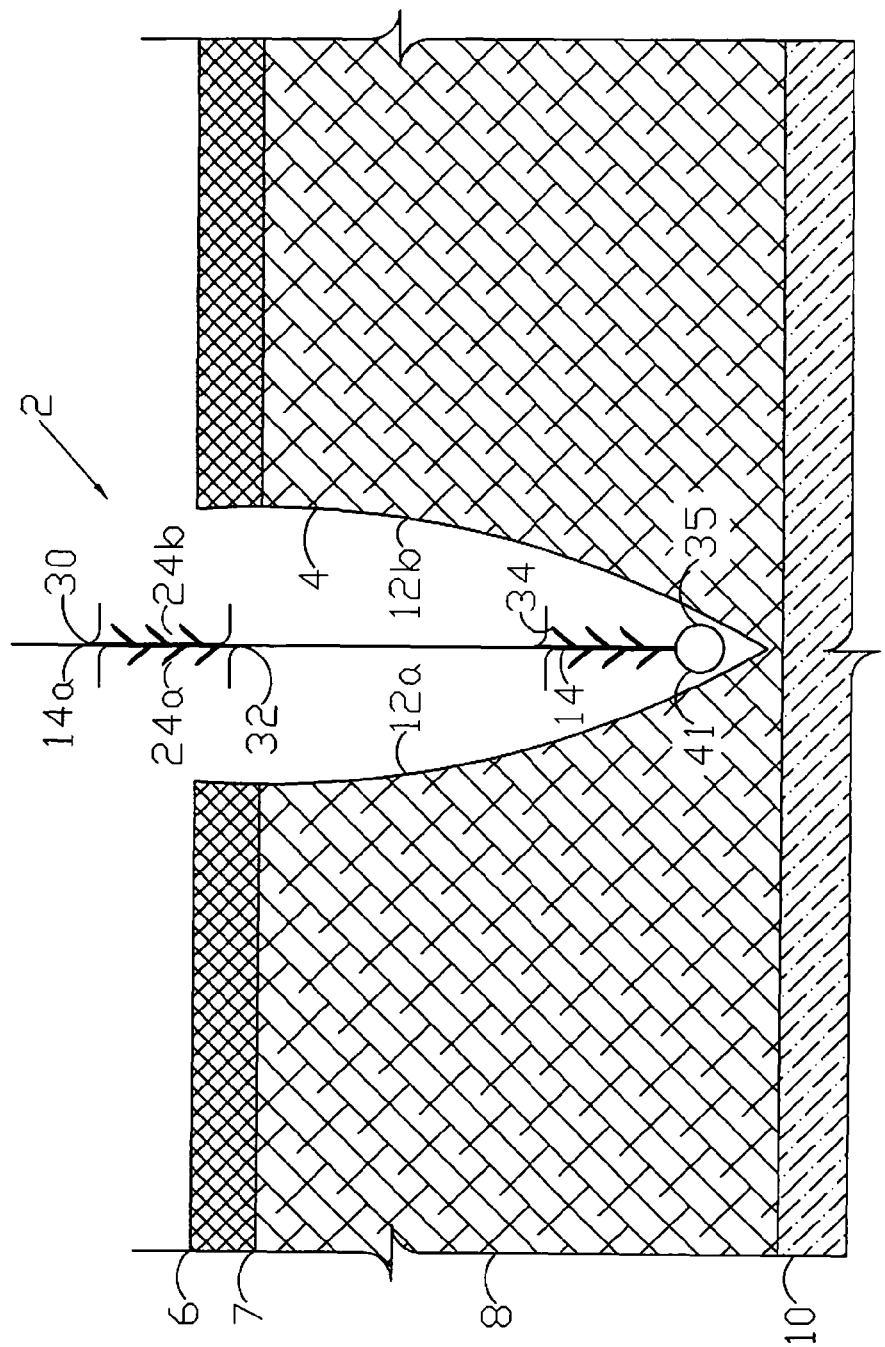

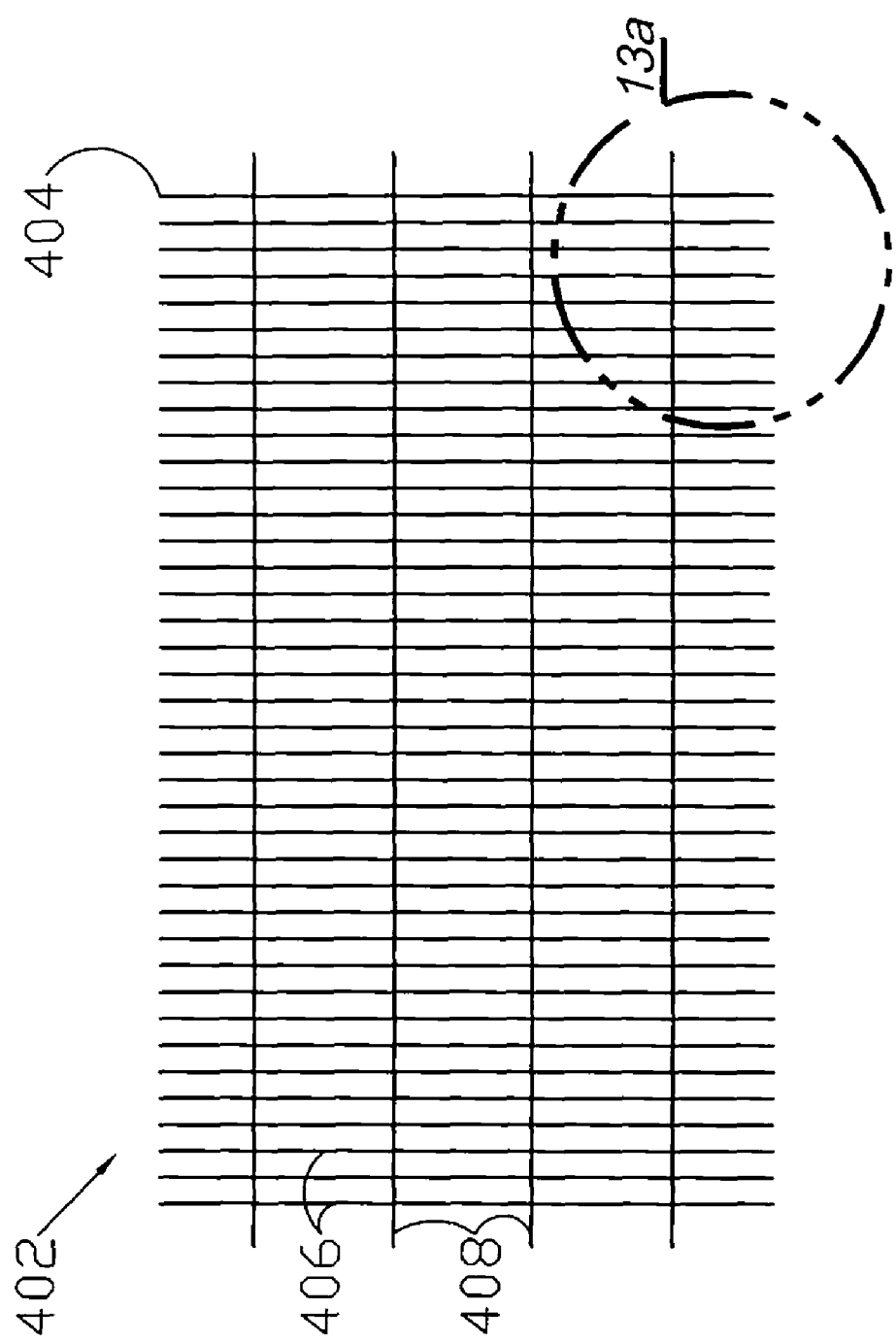

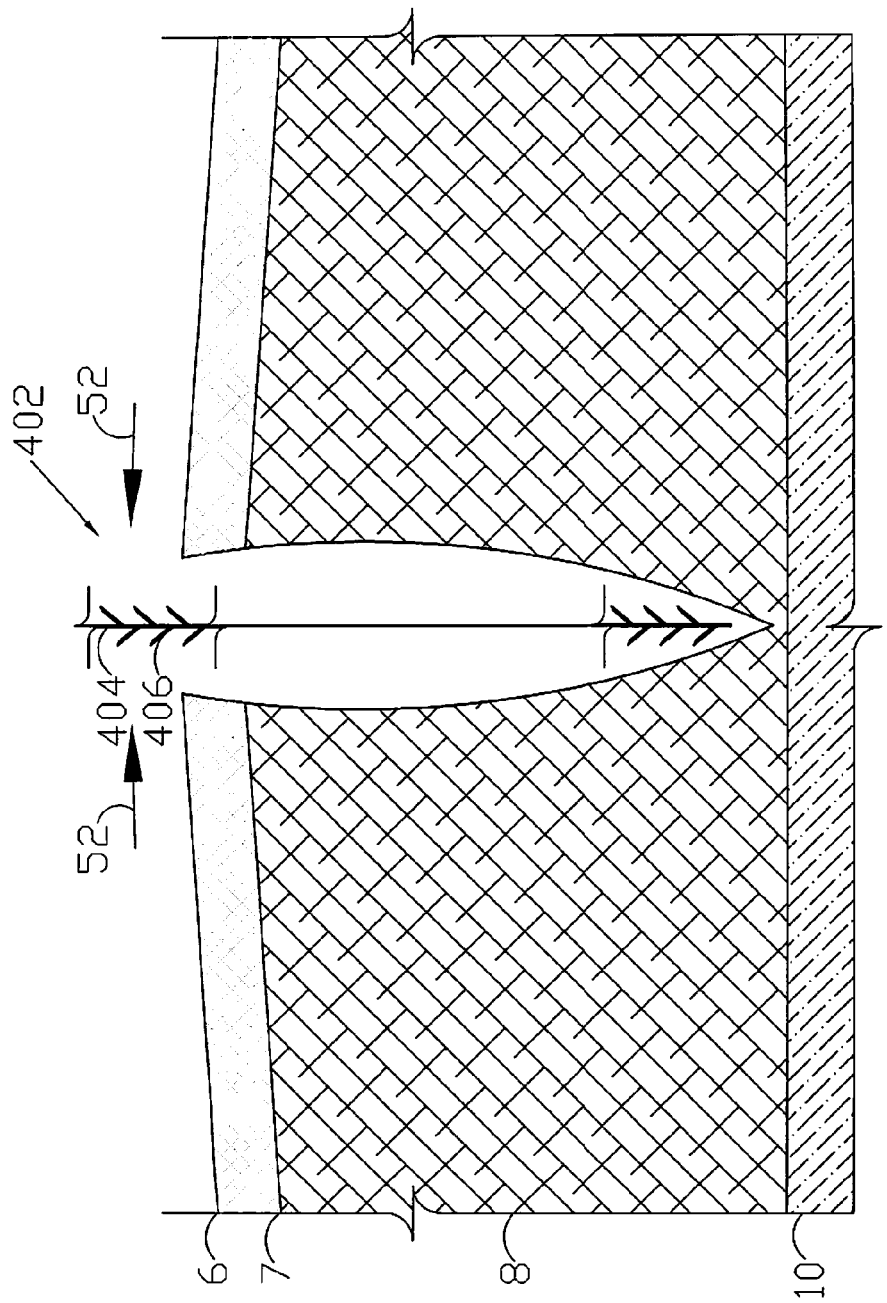

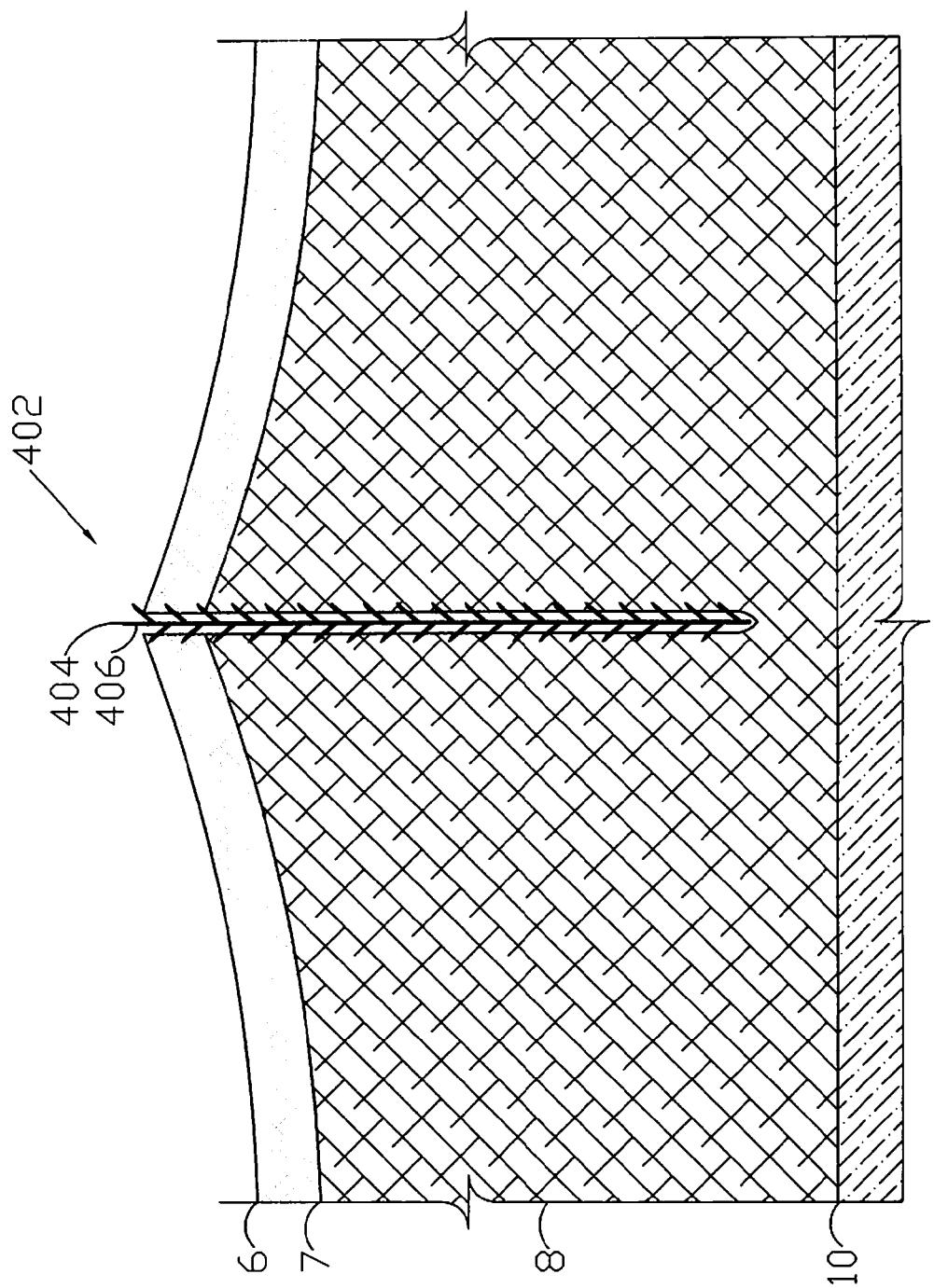

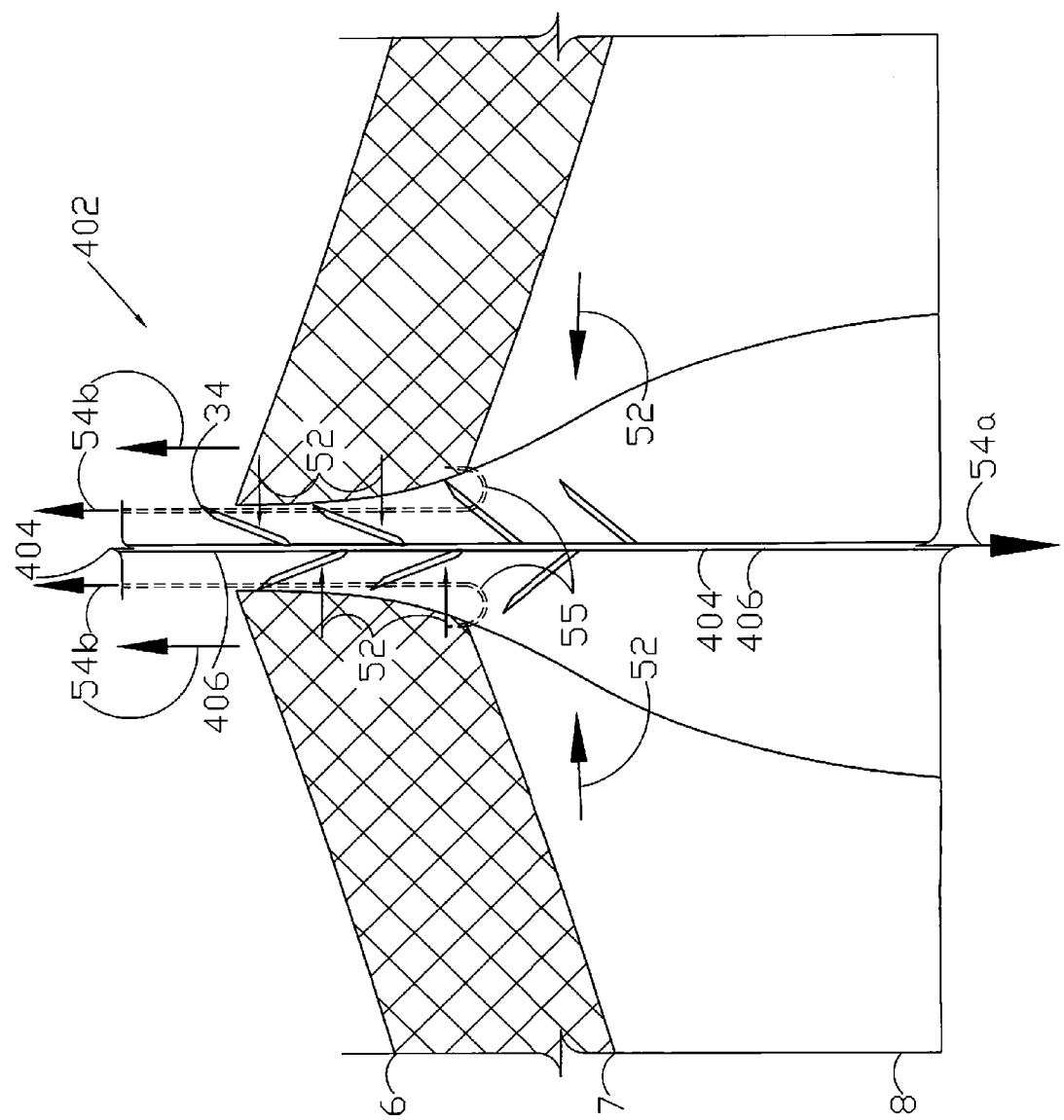

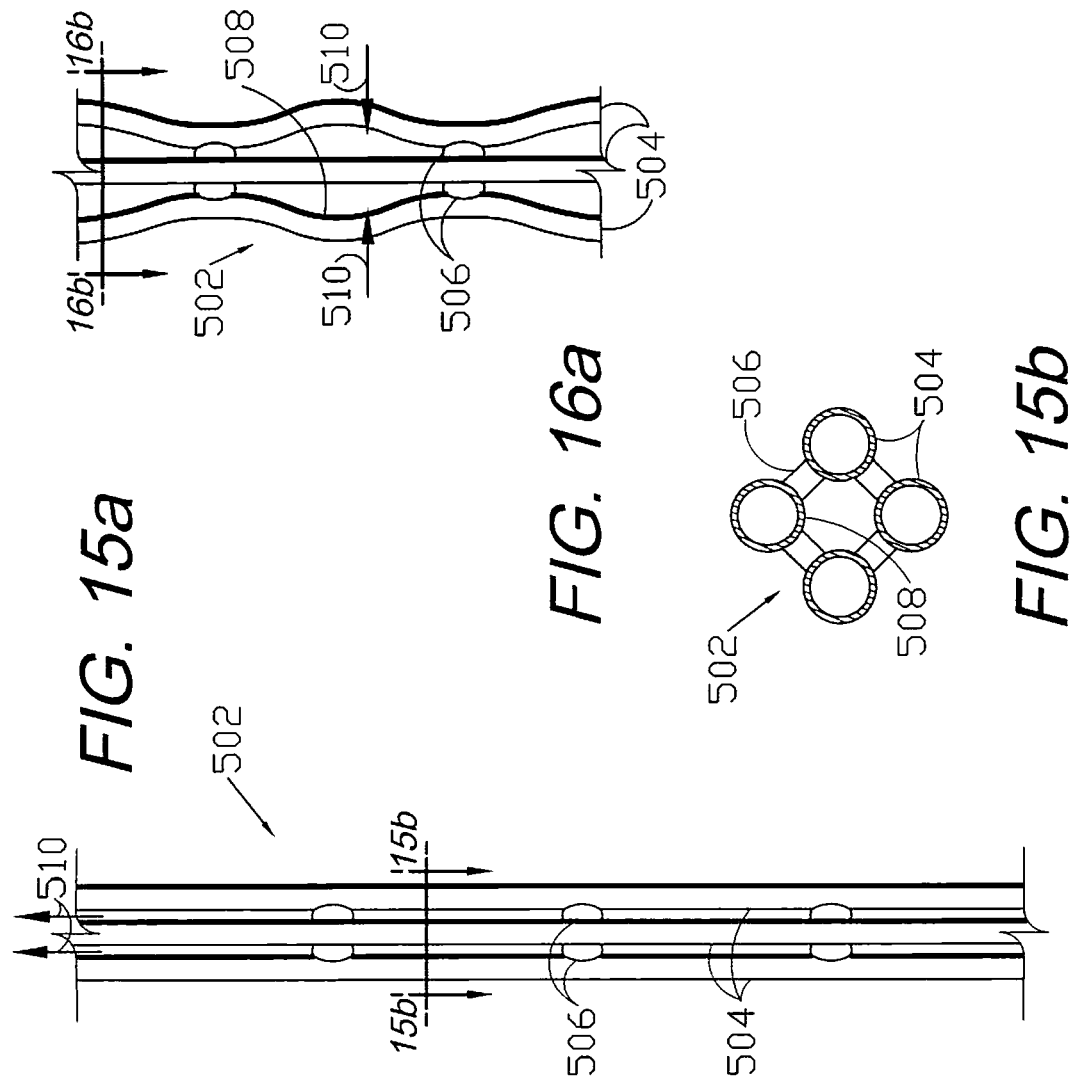

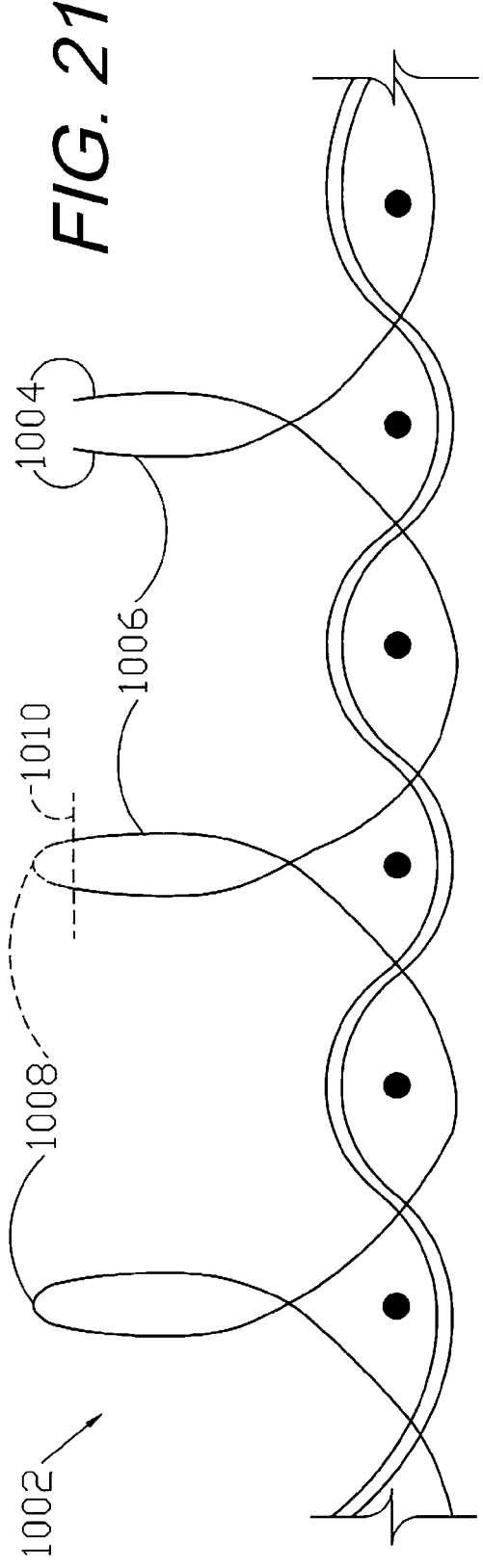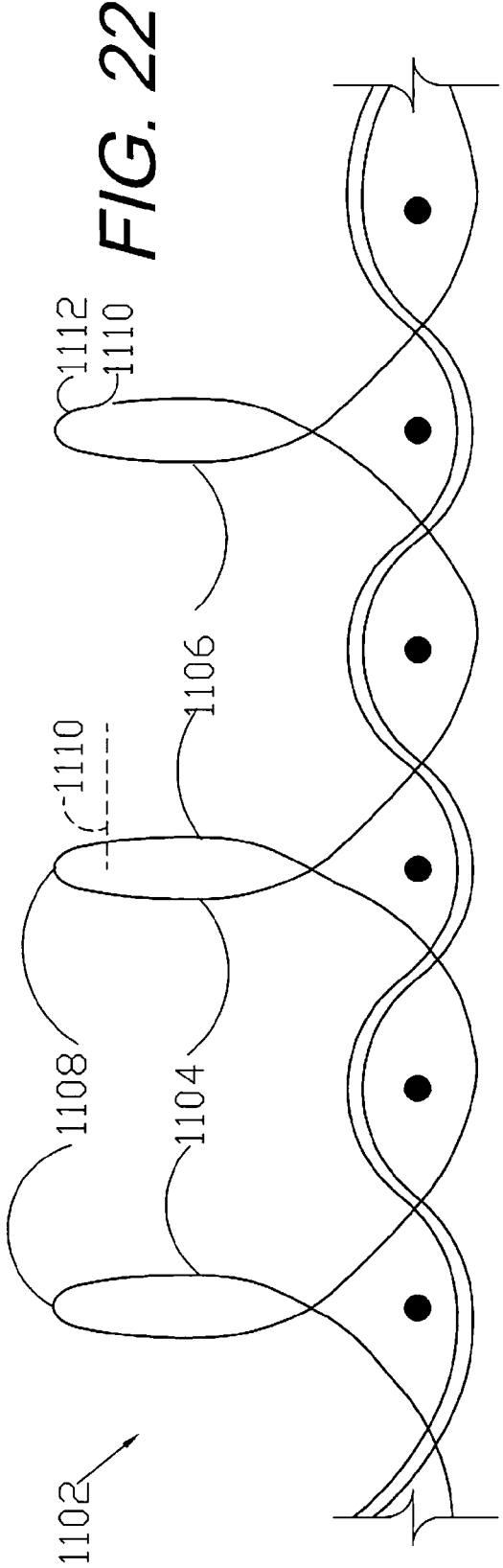

SCREEN DEVICES AND METHODS FOR CLOSING TISSUE SEPARATIONS

CROSS-REFERENCE TO RELATED APPLICATIONS

This application is a continuation and claims priority in application Ser. No. 10/224,852, filed Aug. 21, 2002, now U.S. Pat. No. 7,381,211, dated Jun. 3, 2008. This application also claims priority in application Ser. No. 11/103,056, filed Apr. 11, 2005, now U.S. Pat. No. 7,410,495, application Ser. No. 11/103,052, filed Apr. 11, 2005, now U.S. Pat. No. 7,413,571, application Ser. No. 11/103,403, filed Apr. 11, 2005, now abandoned, and application Ser. No. 11/103,022, filed Apr. 11, 2005, now U.S. Pat. No. 7,413,570, which are continuations-in-part of the same parent application. All of the foregoing applications are incorporated herein by reference.

BACKGROUND OF THE INVENTION

1. Field of the Invention

The present invention relates generally to medical closure and wound fluid management devices, and in particular to an absorbable screen closure member for closing tissue separations, such as incisions and wounds.

2. Description of the Prior Art

In the medical field, cutaneous incisions are commonly performed in surgery to provide access to underlying tissue, organs, joints, skeletal structure, etc. Incision and closure techniques are an important part of surgery in general. They tend to occupy surgical teams and other resources for significant portions of many surgical procedures.

Surgeons generally strive to minimize the traumatic and scarring effects of surgery on their patients by both minimizing the incisions, and by employing a variety of closure techniques which tend to reduce postoperative swelling, bleeding, seroma, infection and other undesirable postoperative side effects. For example, the fields of endoscopic-assisted surgery, microscopic surgery, and computer-enhanced instrumentation (e.g., the DaVinci System available from Intuitive Surgical, Inc. of Sunnyvale, Calif.) are generally concerned with minimally invasive surgery ("MIS") procedures and techniques, which have proven to be increasingly popular. Such popularity is at least partly due not only to the minimally-sized scars left by such techniques, but also to the minimal trauma to the fascia and muscle layers and the correspondingly faster recoveries this allows. However, surgeons must balance such considerations with providing adequate access to perform various surgical procedures.

Some surgical procedures, by their nature, must include long incisions. Examples include cutaneous excisional procedures such as "lifts" and reduction procedures, flap procedures for closure of defects, and many bariatric procedures.

The "first intention" (primary intention healing) in surgery is to "close" the incision. For load-bearing tissues, such as bone, fascia, and muscle, this requires substantial material, be it suture material, staples, or plates and screws. For the wound to be "closed," the epithelial layer must seal. To accomplish this, the "load bearing" areas of the cutaneous and subcutaneous layers (i.e., the deep dermal elastic layer and the superficial fascia or fibrous layers of the adipose tissue, respectively) must also at least be held in approximation. Important considerations include controlling infection and bleeding, reducing scarring, eliminating the potential of hematoma, seroma, and "dead-space" formation and managing pain. Dead space problems are more apt to occur in the subcutaneous closure. Relatively shallow incisions can normally be closed with surface-applied closure techniques, such as sutures, staples, glues, and adhesive tape strips. However, deeper incisions may well require not only skin surface closure, but also time-consuming placement of multiple layers of sutures in the load-bearing planes. Absorbable sutures are commonly used for this purpose and comprise an important class of surgical sutures. Depending on various factors, absorbable sutures typically dissolve over a period of a few days to a few months. Commercially available examples include Monocryl® monofilament absorbable synthetic sutures comprising a poliglecaprone and PDS® (polydrioxanone) and Vicryl® (polyglactin) sutures, all available from Ethicon, Inc., of Somerville, N.J.

Surgical mesh represents another important class of surgical closure devices. Applications include reconstruction, hernia repair, and organ repair. In such procedures, surgical mesh fabric prostheses are inserted into patients through either open surgery or endoscopic (MIS) procedures. Knitted surgical mesh for hernia repair is disclosed in the Agarwal et al. U.S. Pat. No. 6,287,316, which is assigned to Ethicon, Inc. Another Ethicon, Inc. patent, Duncan U.S. Pat. No. 4,548,202, discloses mesh tissue fasteners including various fastening members with spaced-apart legs for passing through tissue portions. Another closure procedure involves the placement of pins or rods through skin edge or bone followed by the placement of an external clamp or fixator device spanning the wound and frequently incorporating a worm-screw apparatus capable of progressive tightening over time to effect closure, stabilization or distraction.

Fluid management represents another important aspect of both open and minimally invasive surgery. Postoperative fluid drainage can be accomplished with various combinations of tubes, sponges, and porous materials adapted for gathering and draining bodily fluids. The prior art includes technologies and methodologies for assisting drainage. For example, the Zamierowski U.S. Pat. No. 4,969,880; No. 5,100,396; No. 5,261,893; No. 5,527,293; and No. 6,071,267 disclose the use of pressure gradients, i.e., vacuum and positive pressure, to assist with fluid drainage from wounds, including surgical incision sites. Such pressure gradients can be established by applying porous sponge material either internally or externally to a wound, covering same with a permeable, semipermeable, or impervious membrane, and connecting a suction vacuum source thereto. Fluid drawn from the patient is collected for disposal. Such fluid control methodologies have been shown to achieve significant improvements in patient healing. Another aspect of fluid management, postoperative and otherwise, relates to the application of fluids to wound sites for purposes of irrigation, infection control, pain control, growth factor application, etc. Wound drainage devices are also used to achieve fixation and immobility of the tissues, thus aiding healing and closure. This can be accomplished by both internal closed wound drainage and external vacuum devices. Fixation of tissues in apposition can also be achieved by bolus tie-over dressings (Stent dressings), taping, strapping and (contact) casting.

Heretofore, there has not been available a medical closure screen with the advantages and features of the present invention, including the combination of same with vacuum-assisted closure.

SUMMARY OF THE INVENTION

In the practice of the present invention, a medical closure screen device is provided, which includes a mesh screen comprising tubular vertical risers, barbed filaments therebetween and horizontal spacers. An optional perimeter member partly surrounds the screen member and can comprise a perimeter tube fluidically coupled with the vertical risers to form a tubing assembly. The tubing assembly cooperates with the vertical risers to extract fluid from the tissue separation in a drain mode and to introduce fluid thereinto in an irrigate mode. In one embodiment of the invention the tubing assembly is fluidically coupled to a vacuum source to facilitate drainage. In another embodiment of the invention, the perimeter tube is passed through the surrounding tissue to secure the screen member in place. Fluid transfer elements, such as sponges, are optionally placed adjacent to and over an extension of the screen for fluid transfer, for example, in conjunction with a vacuum or pump source. Another embodiment of the invention includes a suture connected to the screen and adapted for securing same in a tissue separation. Alternative embodiment vertical risers are also disclosed, and can provide active fluid transfer utilizing the patient's body dynamics. Yet another alternative embodiment of the present invention utilizes the screen barbs for mechanical fixation in a separation for closure of same. Separation closure, irrigation and drainage methodologies are disclosed utilizing various combinations of closure screens, tubing, sutures, fluid transfer elements and gradient force sources. The closure screen of the present invention uses mechanical and other forces associated with screens and barbed strands for securing separated tissues together and for eliminating or reducing the formation of subcutaneous voids or pockets, which can potentially form hematoma and seroma effects.

BRIEF DESCRIPTION OF THE DRAWINGS

FIG. 2 is an enlarged, fragmentary, side elevational view thereof, taken generally within circle 2 in FIG. 1.

FIG. 3 is an enlarged, fragmentary, side elevational view thereof, taken generally along line 3-3 in FIG. 2, and particularly showing a barbed strand.

FIGS. 4a-f show alternative perimeter tube end closures comprising: 4a) subdermal termination; 4b) knotted end; 4c) Leur lock; 4d) transfer element (i.e., sponge); 4e) vacuum source; and 4f) clamped end.

FIGS. 5a-e show a tissue separation closure procedure embodying the method of the present invention.

FIG. 12 is a side elevational view of a screen-only closure screen comprising an alternative embodiment of the present invention.

FIGS. 14a-g show a tissue separation closure procedure utilizing the screen-only embodiment of the closure screen.

FIG. 15a is a side elevational view of a modified vertical riser with flexible, multi-tube risers forming a fluid passage.

FIG. 15b is a cross-sectional view thereof, taken generally along line 15b-15b in FIG. 15a.

FIG. 16a is a fragmentary, side elevational view thereof, shown in a compressed configuration.

FIG. 16b is a cross-sectional view thereof, taken generally along line 16b-16b in FIG. 16a.

FIG. 17 is a cross-sectional view of another modified vertical riser construction with risers bundled in a different configuration, with barbs.

FIG. 21 is an enlarged, cross-sectional view of a closure screen comprising an alternative embodiment of the present invention, with barbs formed by cutting off the ends of looped filaments.

FIG. 22 is an enlarged, cross-sectional view of a closure screen comprising an alternative embodiment of the present invention, with barbs forming hooks and constructed by cutting looped filaments.

DETAILED DESCRIPTION OF THE PREFERRED EMBODIMENTS

I. Introduction and Environment

Figure 1:
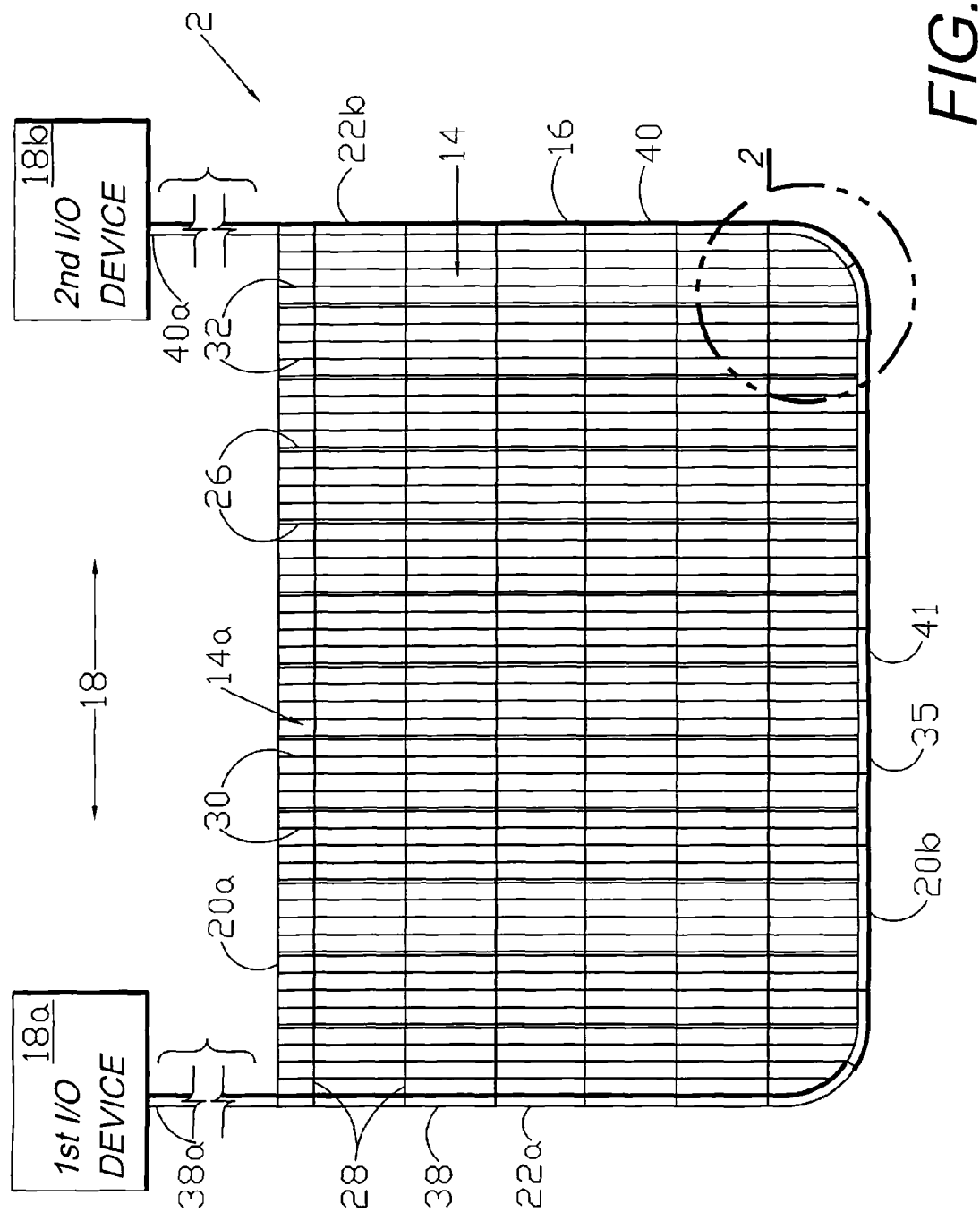
FIG. 1 is a side elevational view of a medical closure screen device embodying the present invention.

As required, detailed embodiments of the present invention are disclosed herein; however, it is to be understood that the disclosed embodiments are merely exemplary of the invention, which may be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure.

Certain terminology will be used in the following description for convenience in reference only and will not be limiting. For example, the words "upwardly", "downwardly", "rightwardly" and "leftwardly" will refer to directions in the drawings to which reference is made. The words "inwardly" and "outwardly" will refer to directions toward and away from, respectively, the geometric center of the embodiment being described and designated parts thereof. The words "horizontal" and "vertical" generally mean side-to-side and end-to-end, respectively. Said terminology will include the words specifically mentioned, derivatives thereof and words of a similar import.

Referring to the drawings in more detail, the reference numeral 2 generally designates a medical closure screen device or system embodying the present invention. Without limitation on the generality of useful applications of the closure screen system 2, the primary application disclosed herein is for assistance with the closing, draining, irrigating and healing of a separation of first and second tissue portions, such as a wound or incision 4. As shown in FIG. 5a, the wound 4 extends from and is open at the dermis 6, through the deep dermal layer 7 and the subcutaneous layer 8, and to approximately the fascia 10. The wound 4 displays edges 12a,b, which correspond to first and second tissue portions. The closure screen device 2 generally comprises a screen 14, a screen perimeter member 16 and an input/output (I/O) subsystem 18.

II. Screen 14

The screen 14 includes upper and lower margins 20a,b; first and second ends 22a,b; and first and second faces 24a,b. The screen 14 generally forms a grid configuration with vertical, hollow, perforated tubular risers 26 cross-connected by horizontal spacer members 28. Multiple barbed strands 30 are positioned between the risers 26. The risers 26, the spacers 28 and the strands 30 are preferably joined at their respective intersections. As shown in FIG. 3, each strand 30 includes a filament 32 with multiple, pointed barbs 34 extending upwardly and outwardly on both sides in staggered, spaced relation. The barbs 34 generally project outwardly from the screen faces 24a,b, for purposes which will be described in more detail hereinafter.

The screen or mesh 14 material can be either dissolvable (absorbable) or non-dissolvable (non-absorbable) and can be chosen from a number of commercially-available, biocompatible products, which are commonly used in medical applications for sutures, implantable meshes, and similar medical devices.

Examples of absorbable materials include, but are not limited to: aliphatic polyesters, which include, but are not limited to: homo polymers and copolymers of lactide, .epsilon.-caprolactone, p-dioxanone, trimethylene carbonate, alkyl derivatives of trimethylene carbonate, .delta.-hydroxyvalerate, 1,4-dioxepan-2-one, 1,5-dioxepan-2-one, 6,6-dimethyl-1,4-dioxan-2-one and polymer blends thereof. Examples of nonabsorbable materials include, but are not limited to: cotton, linen, silk, polyamides, polyesters, fluoropolymers, polyolefins, polyethylene and combinations thereof.

III. Screen Perimeter Member 16

The optional screen perimeter member 16 can comprise, for example, a flexible, perforated, hollow tube 35 with multiple orifices 36. As shown in FIG. 1, the tube 35 includes first and second legs 38, 40 extending generally along the screen first and second ends 22a,b, and a base leg 41 extending generally along the screen lower margin 20b. The tubing first and second legs 38, 40 terminate in respective first and second ends 38a, 40a. The tube 35 can be secured to the screen 14 by multiple ties 42, which can comprise extensions of the horizontal spacer members 28 and the strands 30. By providing dissolvable ties 42, the tube 35 can be designed for separation from the remainder of the closure screen 2 after a relatively short period of time. For example, the dissolvable material can dissolve into the patient's body after a few days, whereafter the tube 35 can be removed.

Optionally, portions of the tube 35 can be cut away from the screen 14. For example, the screen 14 can be separated along each screen end 22a,b, or it can be separated completely from the tube 35. In this manner the screen 14 and the tube 35 can be configured to accommodate a variety of conditions and tissue separation configurations.

The vertical risers 26 are optionally fluidically coupled to the tube 35 at respective T intersections 44. In this configuration the tube 35 and the vertical risers 26 cooperate to provide a manifold for fluid handling, i.e. either extraction or irrigation, as indicated by the fluid flow arrows 45.

IV. Input/Output (I/O) Subsystem 18

The input/output subsystem 18 is designed for extraction and/or irrigation of the patient's bodily fluids and/or external fluids. As shown in FIG. 1, the input/output subsystem 18 includes first and second I/O devices 18a,b attached to the tubing first and second leg ends 38a,b, which in this configuration are considered the "port" ends of the tube 35. One or both of the I/O devices 18a,b can comprise a pressure differential source, such as a VAC® (Vacuum Assisted Closure) unit available from Kinetic Concepts, Inc. of San Antonio, Tex. The use of such units for wound treatment and fluid management is disclosed in the Zamierowski U.S. Pat. No. 4,969,880; No. 5,100,396; No. 5,261,893; No. 5,527,293; and No. 6,071,267, which are incorporated herein by reference.

Alternatively, the tubing port ends 38a,b can be connected to various other sources of pressure differential and various drainage and irrigation devices. For example, they can be cut short below the dermis 6 and left within the separation 4 for sealing by the adjacent tissue portions 12a,b. FIG. 4a shows a truncated tubing end 38b. The tubing ends 38a/40a can be knotted (as shown at 48 in FIG. 4b), clipped, tied (e.g., with a suture) or otherwise closed off either above or below the dermis 6. FIG. 4c shows a Leur lock coupling 46 mounted on a tubing end 38a/40a. Still further, a transfer element comprising a piece of foam or sponge 50 can be coupled to the tube 35 at an end 38a/40a (FIG. 4d). Examples of such foam and sponge materials and configurations are discussed in the Zamierowski U.S. patents identified above. A pressure differential source, such as a vacuum source 51, can be connected to a tube end 38a/40a and to a fluid receptacle 66, as shown in FIG. 4e. A clamp 62 is shown in FIG. 4f and closes the tube end 38a/40a. The clamp 62 can be chosen from among several suitable clamps, which are commonly used for medical applications.

Either tube end 38a/40a can function as either an inlet port or an outlet port with respect to the system 2. For example, suction can be applied for pulling fluid from the patient through the system 2 through either tube end 38a/40a. Still further, fluid can be pulled in both directions through the system 2 by alternately or jointly applying suction to the tube ends 38a/40a. For example, suction can be simultaneously applied to both tube ends 38a/40a.

V. Operation and Closure Method

Figure 5B:
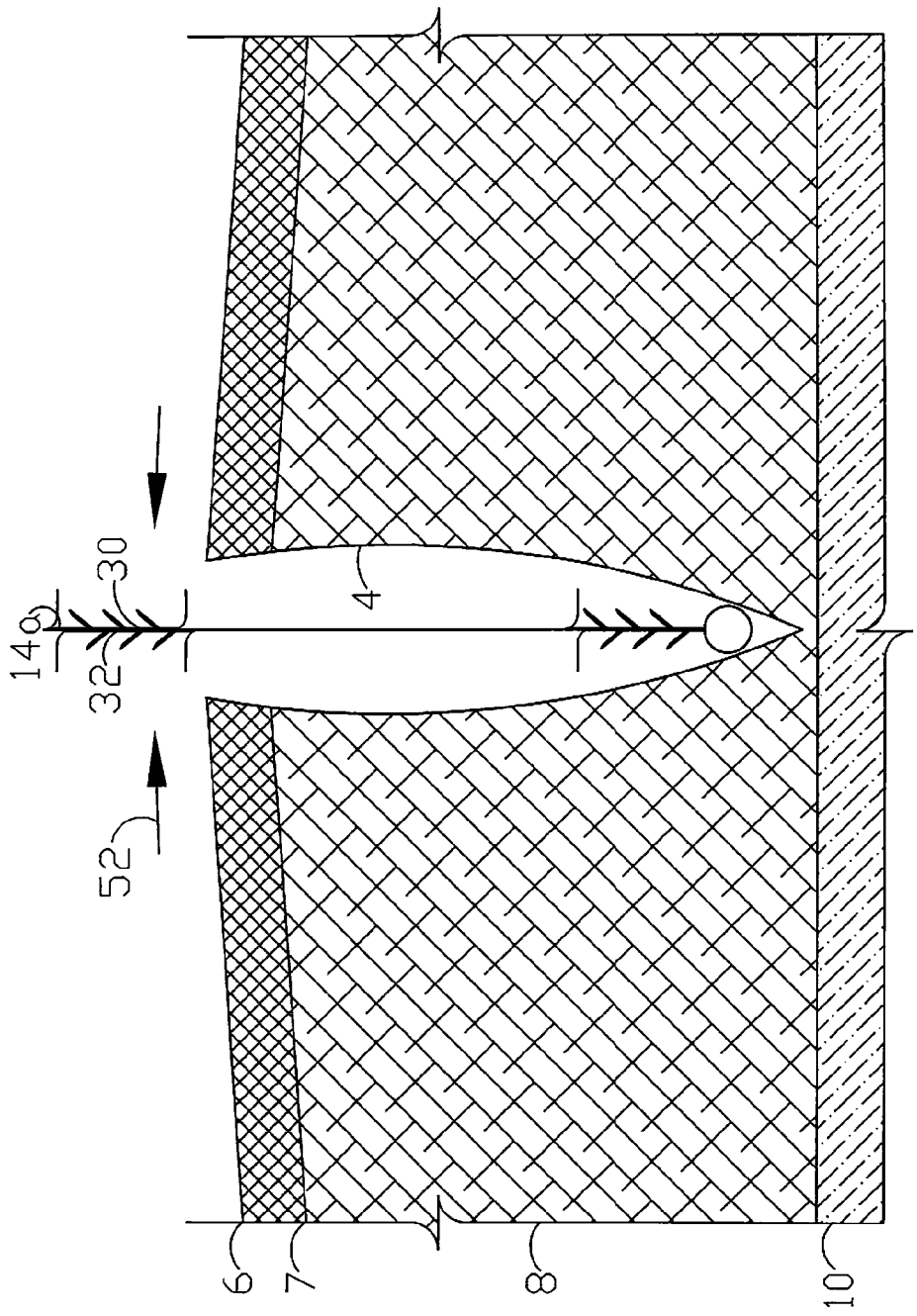
Figure 5C:
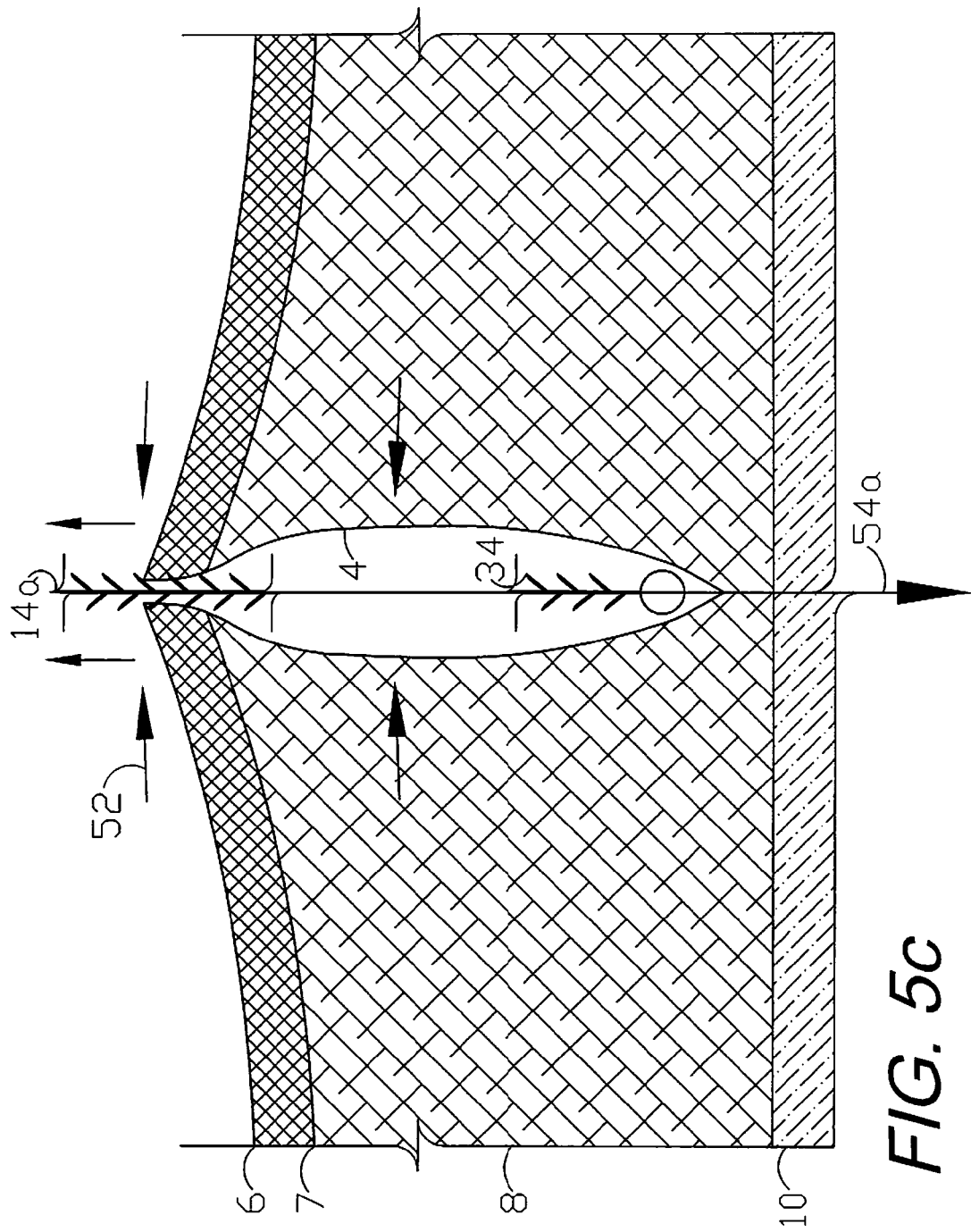
Figure 5D:
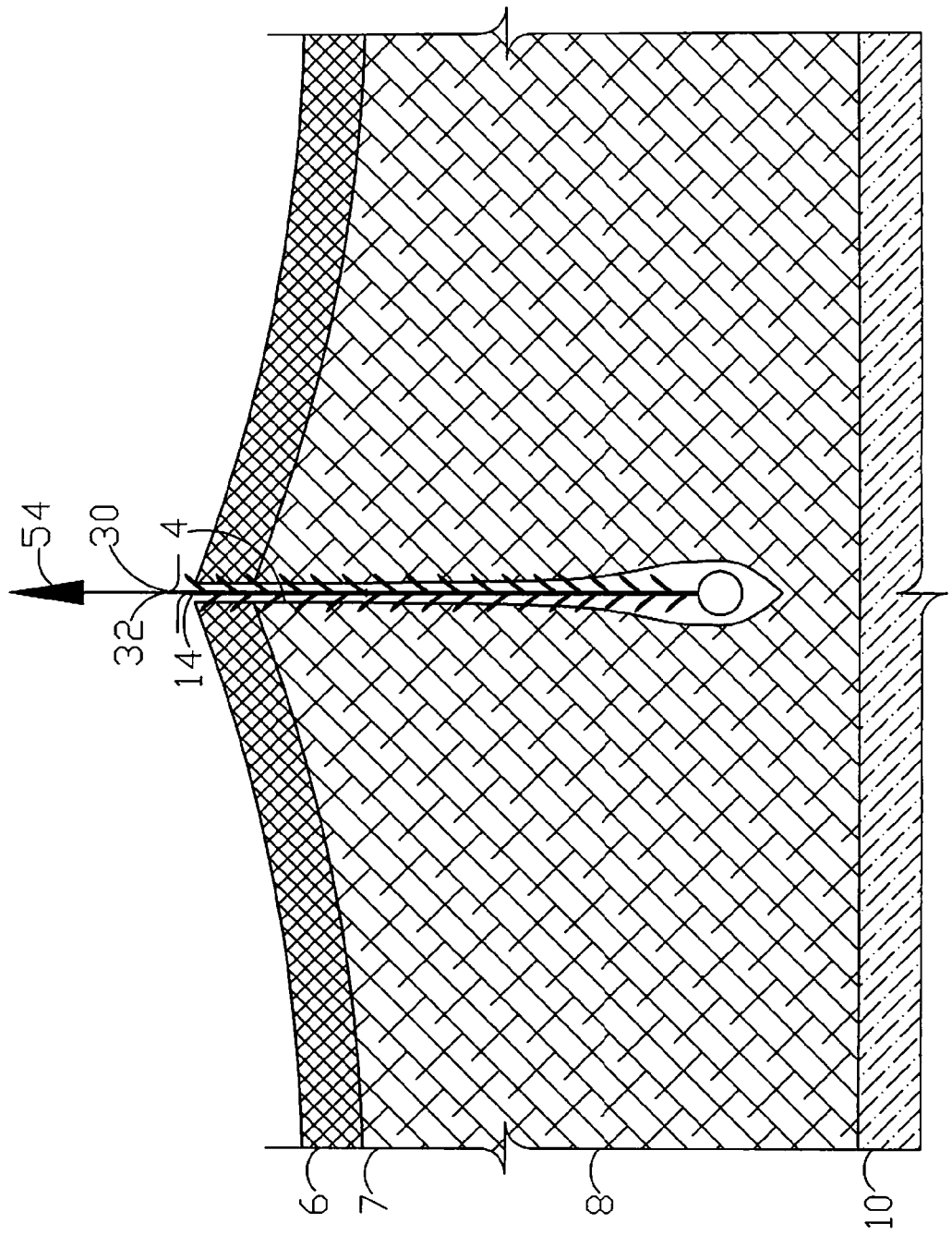

FIGS. 5a-e show an installation methodology utilizing the system 2 of the present invention. In FIG. 5a, the closure screen 2 is placed in the separation 4 with the tubing base 41 located at the bottom of the separation (e.g., wound or incision) 4 and in proximity to the fascia layer 10. As shown, the tissue portions or wound/incision edges 12a,b are spaced apart. The screen upper margin 20a can protrude outwardly from the dermis 6. FIG. 5b shows the tissue separation edges 12 being pushed together as indicated by the force arrows 52. FIG. 5c shows the separation edges 12 engaged at the dermis 6, and spaced apart somewhat within the subcutaneous layer 8. The edges 12 can be pushed together as indicated by the force arrows 52. Moreover, the screen 2 can be held or positioned inwardly in order to advance the barbs 34 in the separation edges 12, as indicated by the inward or downward force arrows 54a. FIG. 5d shows the separation edges 12a,b substantially closed on the screen 2. Tugging on the screen 14 in the general direction of the outward force arrow 54b sets the mesh barbs 34.

Figure 5E:
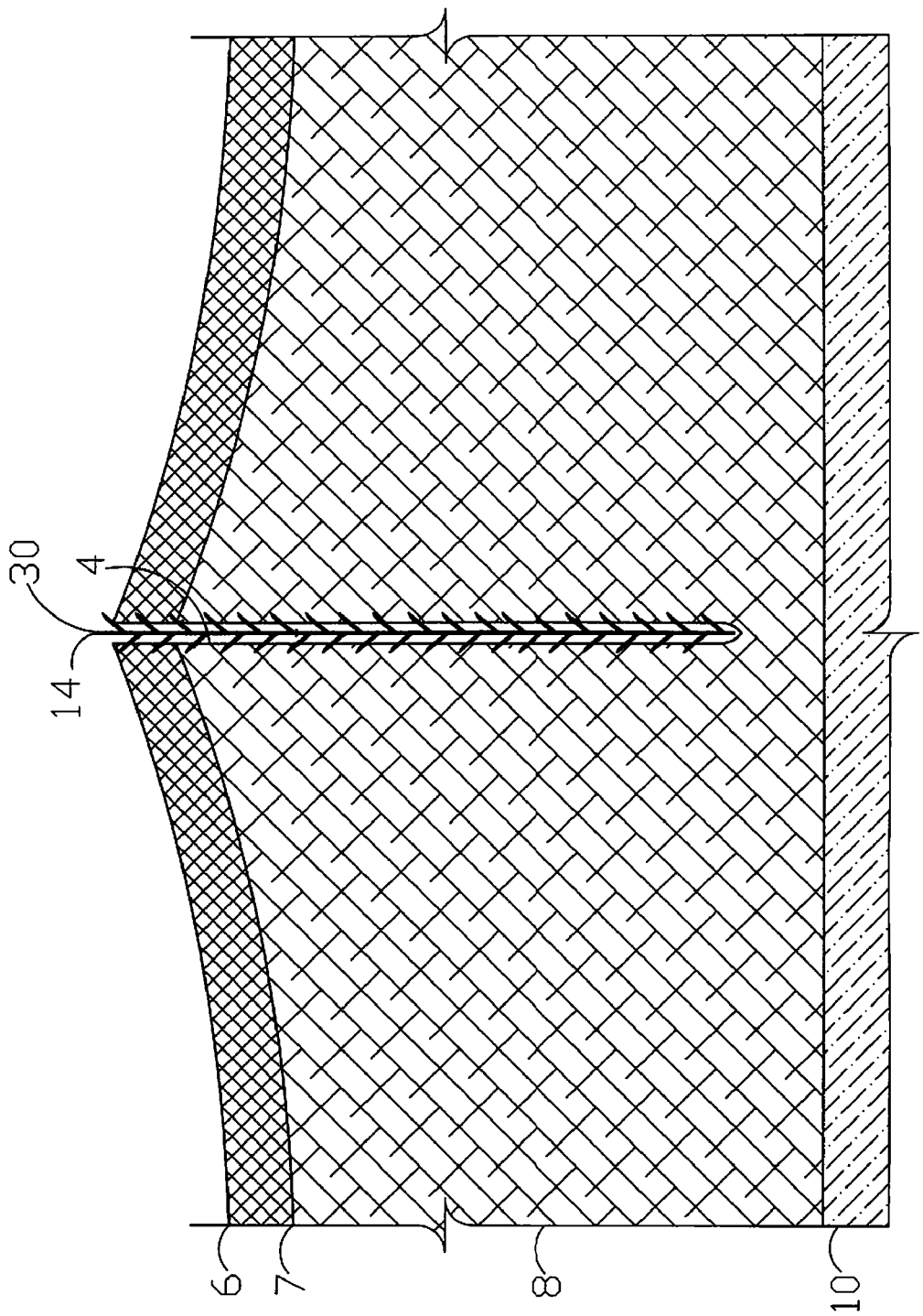

FIG. 5e shows the separation 4 closed on the closure screen 2, with the tubing 35 removed from the screen 14. The tubing 35 can be removed either pre-installation by cutting the ties 42, or post-installation by allowing the ties 42 to dissolve, whereafter the unsecured tubing 35 can be extracted.

Figure 6A:
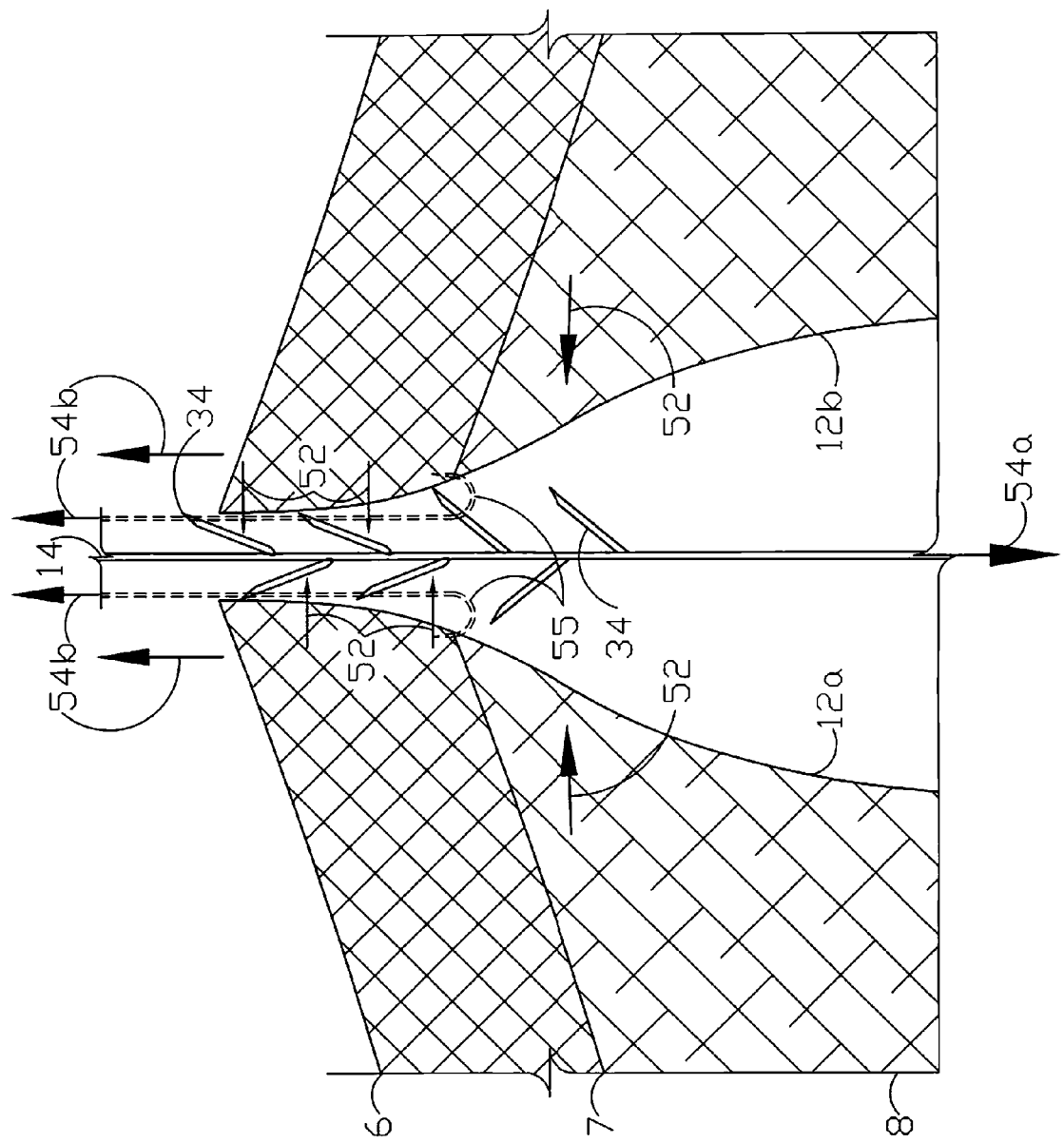
FIG. 6a is an enlarged, fragmentary, cross-sectional view of the closure screen in a tissue separation, with skin hooks shown in hidden lines for positioning the separated tissue portions along the closure screen.
Figure 6B:
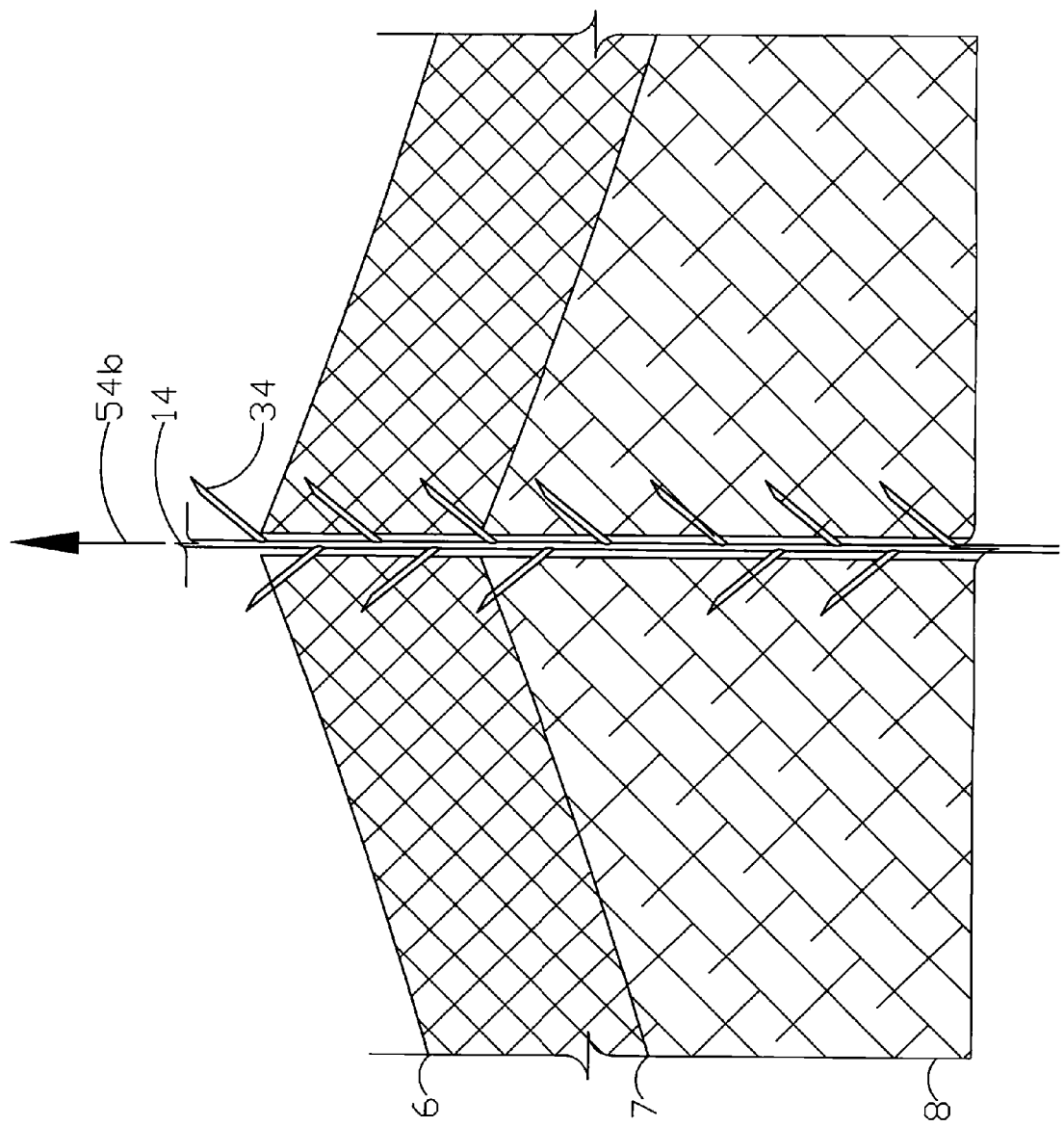
FIG. 6b is an enlarged, fragmentary, cross-sectional view of the closure screen in a substantially closed tissue separation.

FIG. 6a shows the barbs 34 compressed by engagement with the separation edges 12a,b. As shown, the separation edges 12 can be manually closed by pressing along the horizontal force arrows 52. The barbs 34 thus deflect inwardly due to their flexibility, thereby allowing the separation edges 12a,b to slide upwardly or outwardly along the screen 14. This process can be repeated until the separation 4 is closed, as shown in FIG. 6b. Any protruding length of the screen 14 can be cut close to the dermis 6. In the final configuration (FIGS. 5e and 6b), the barbs 34 are embedded in the tissue adjacent to the separation edges 12a,b and thus secure the separation 4 in a closed position. The fluid conducting properties of the screen 14 facilitate extracting fluid. An outward or upward force arrow 54b indicates a force direction whereby the screen barbs 34 are set in the adjoining tissue. It will be appreciated that the screen 14 can be securely set in place with the barbs 34, yet the separation edges 12a,b will remain capable of sliding up on the screen 14 by disengaging the barbs 34 with lateral forces, as shown in FIG. 6a. Skin hooks 55 can be used for engaging the tissue portions 12a,b and tugging same outwardly as shown in FIG. 6a. The skin hooks 55 can facilitate positioning and repositioning the screen 14.

VI. Alternative Embodiment Closure Screen Systems and Methodologies

Figure 7A:
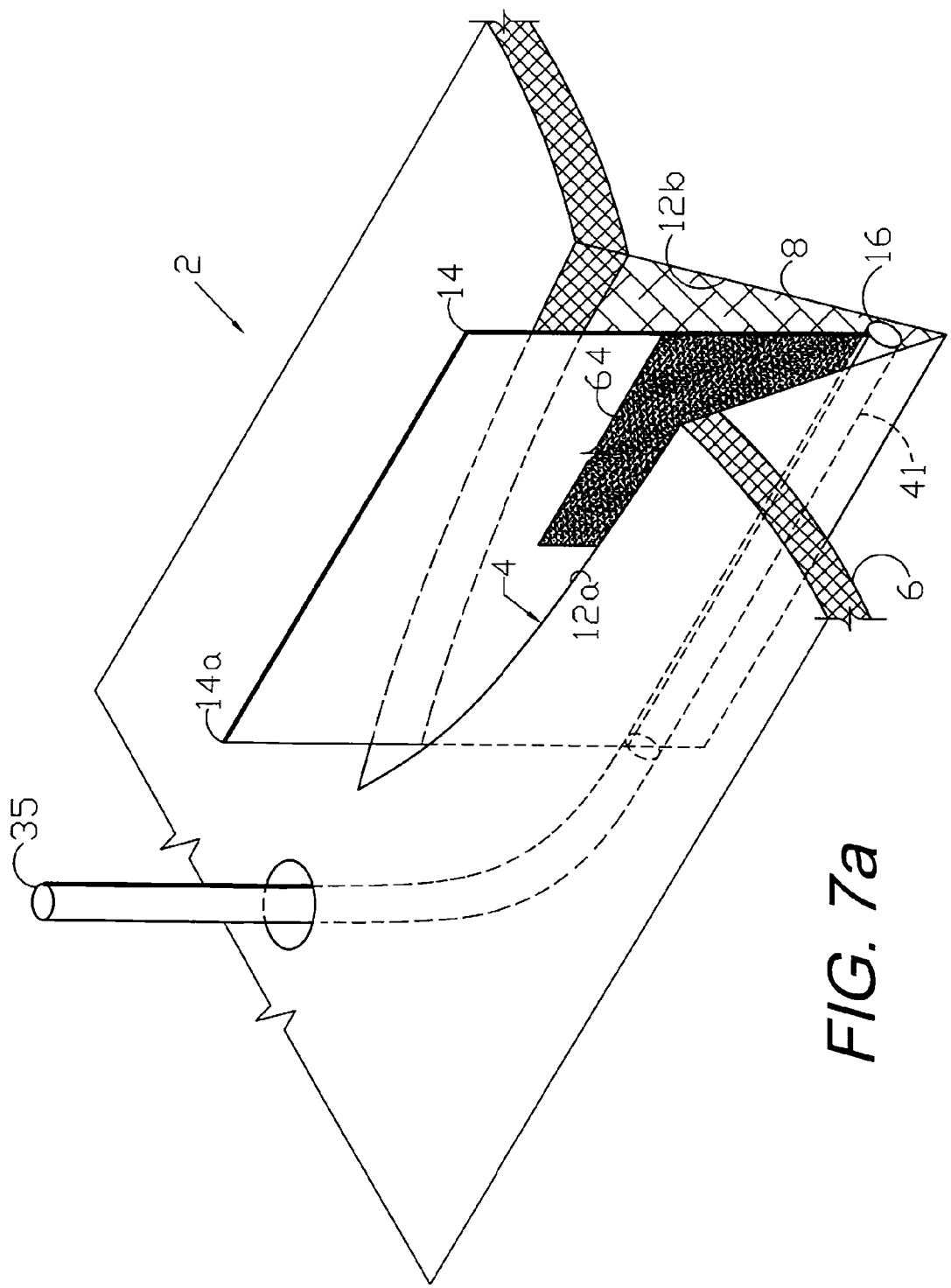
FIGS. 7a-f show a tissue separation closure procedure embodying the method of the present invention and utilizing optional sponge or foam fluid transfer elements and a tubing placement tool.
Figure 7B:
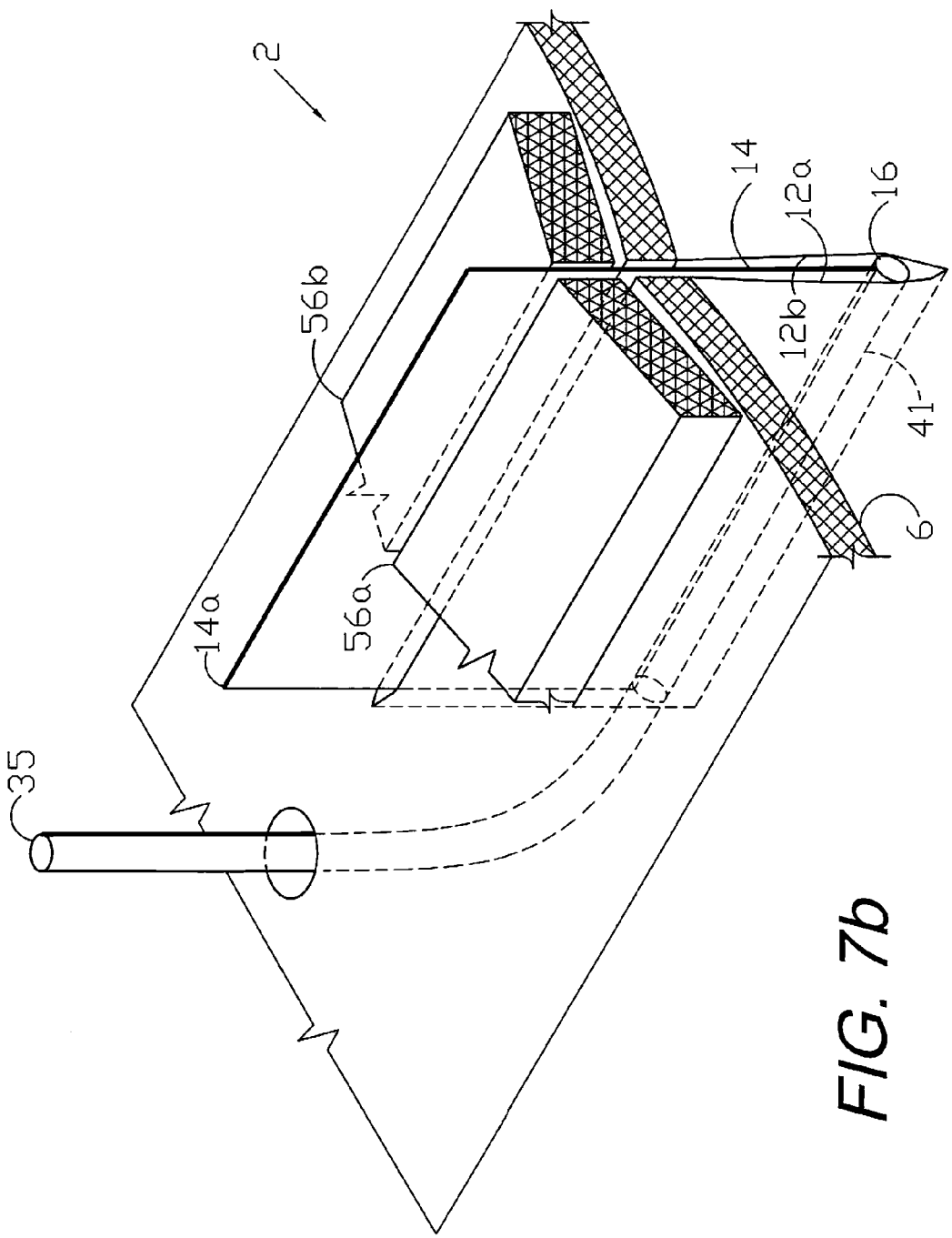

FIGS. 7a-f show an alternative procedure for mounting the closure screen 2 in a wound drainage application utilizing pressure differential. As shown in FIG. 7a, the tubing 35 can pass through the tissue adjacent to the wound 4 and exit the dermis 6 for termination of the tubing end 38a/40a as described above. An optional layer of a suitable, biocompatible adhesive 64 is shown applied to the closure screen first face 24a for securing same to the first wound edge 12a. FIG. 7b shows the screen 14 extending upwardly from the dermis 6 with the wound edges 12a,b brought together in a manner similar to that described above.

Figure 7C:
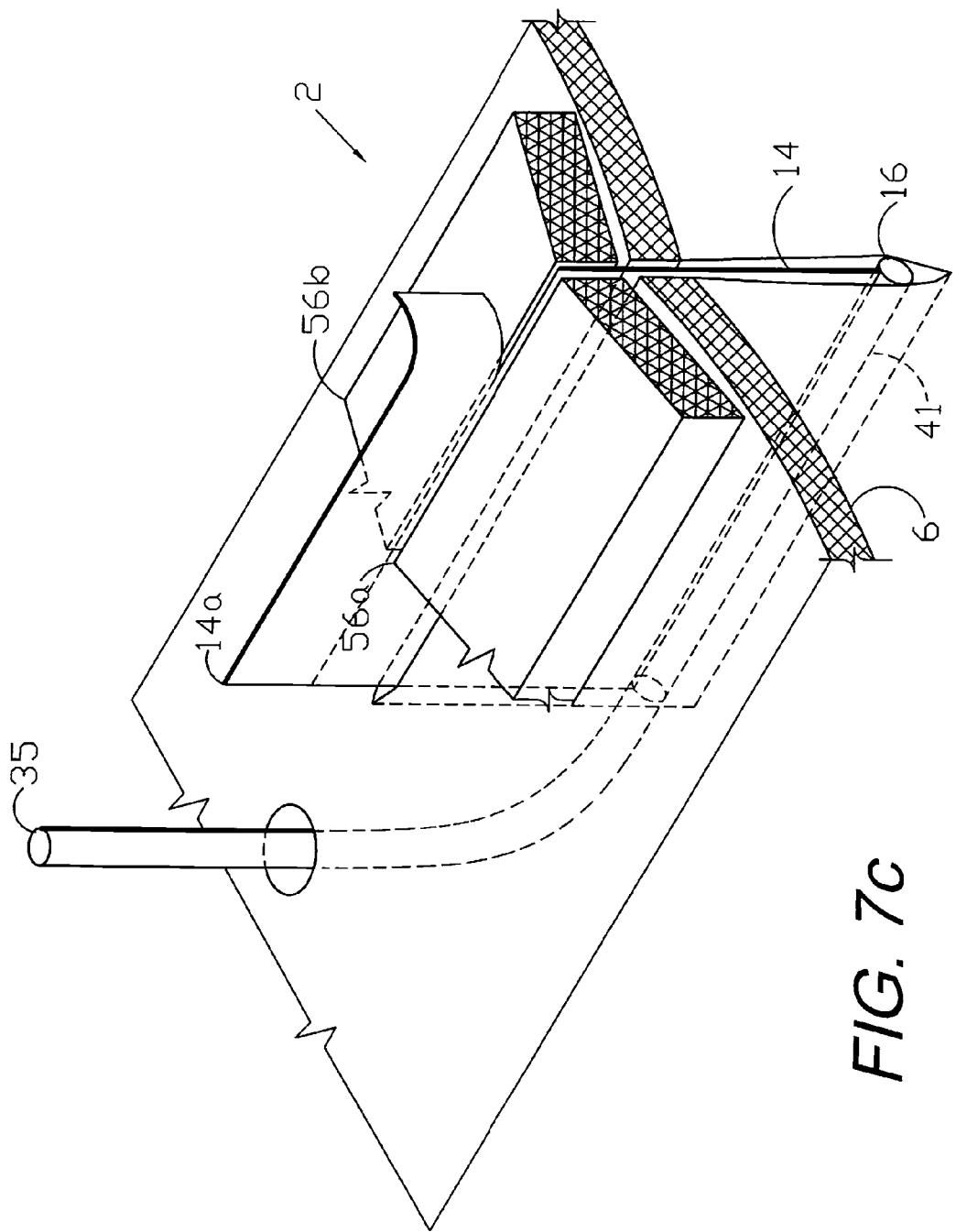
Figure 7D:
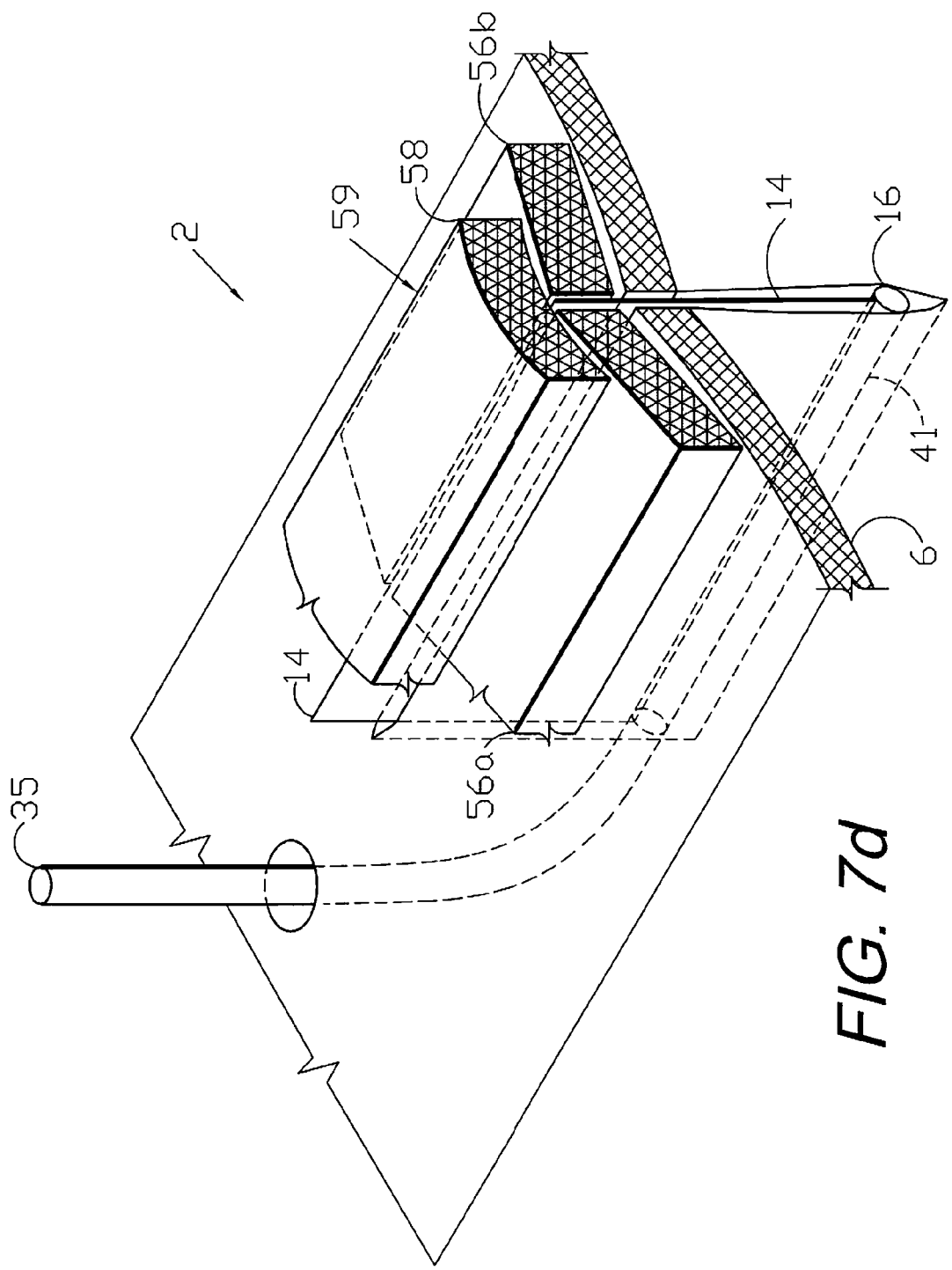

The input/output subsystem 18 includes a pair of optional fluid transfer elements comprising foam or sponge members 56a,b placed on the dermis 6 on either side of a protruding portion 14a of the screen 14. The screen 14 is then cut to a level generally flush with the upper surfaces of the sponges 56a,b, as shown in FIG. 7c. An optional sponge bridge 58 is placed over the sponge members 56a,b (FIG. 7d). Examples of suitable transfer element materials are discussed in the Zamierowski patents noted above and include open-cell, porous foam materials (e.g., polyurethane ester (PUE)) chosen for their hydrophobic properties and passage of liquids. Polyvinyl acetate (PVA) material can be used for its hydrophilic properties. The transfer element subassembly 59 formed by the sponge members 56a,b and 58 can be connected to a vacuum source, a fluid irrigation source, etc. Moreover, it can be connected to additional fluid transfer elements and covered with various flexible membranes and drapes, which can be semi-permeable or impervious, as indicated for the closure and treatment of particular separations and wounds.

Figures 7E, 7F, 9:
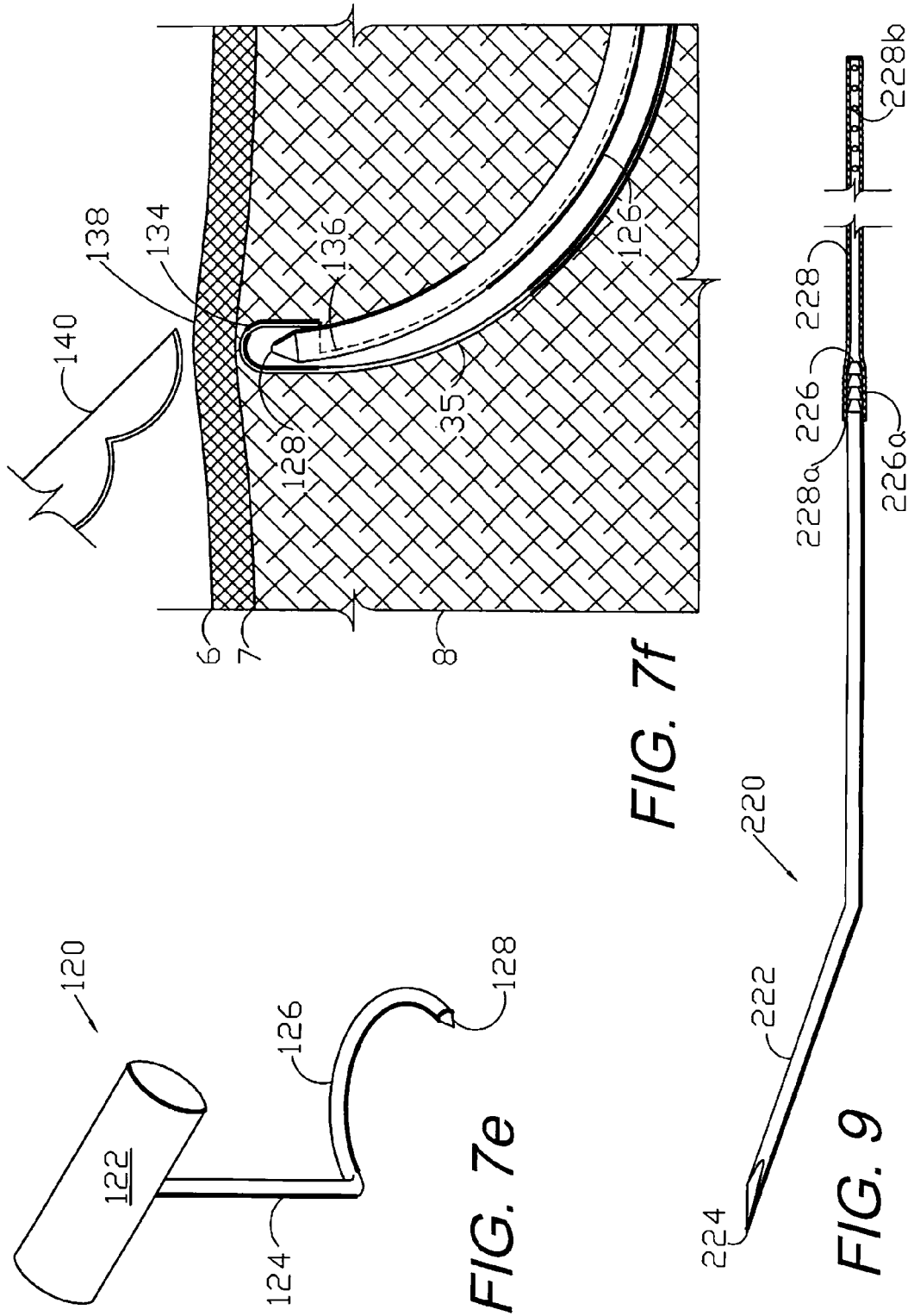
FIG. 9 shows a needle mounting a length of drain tubing and adapted for passing same through tissue.

FIG. 7e shows a tubing placement tool 120 with a handle 122, a shaft 124 and a hook 126 terminating at a pointed or rounded, bullet-shaped tip 128. FIG. 7f shows the tool 120 passing tubing 35 through tissue in the subcutaneous layer 8 and into proximity with the dermis 6. The tip 128 is received in a blind end 134 of the tubing 35 through a notch 136 formed therein. The thrust of the tool 120 causes tenting of the dermis 6, as shown at 138, whereat the dermis 6 can be opened with a scalpel 140 and the tubing 35 can exit the patient for suitable termination arrangements, such as those shown in FIGS. 4a-f above.

Figure 8:
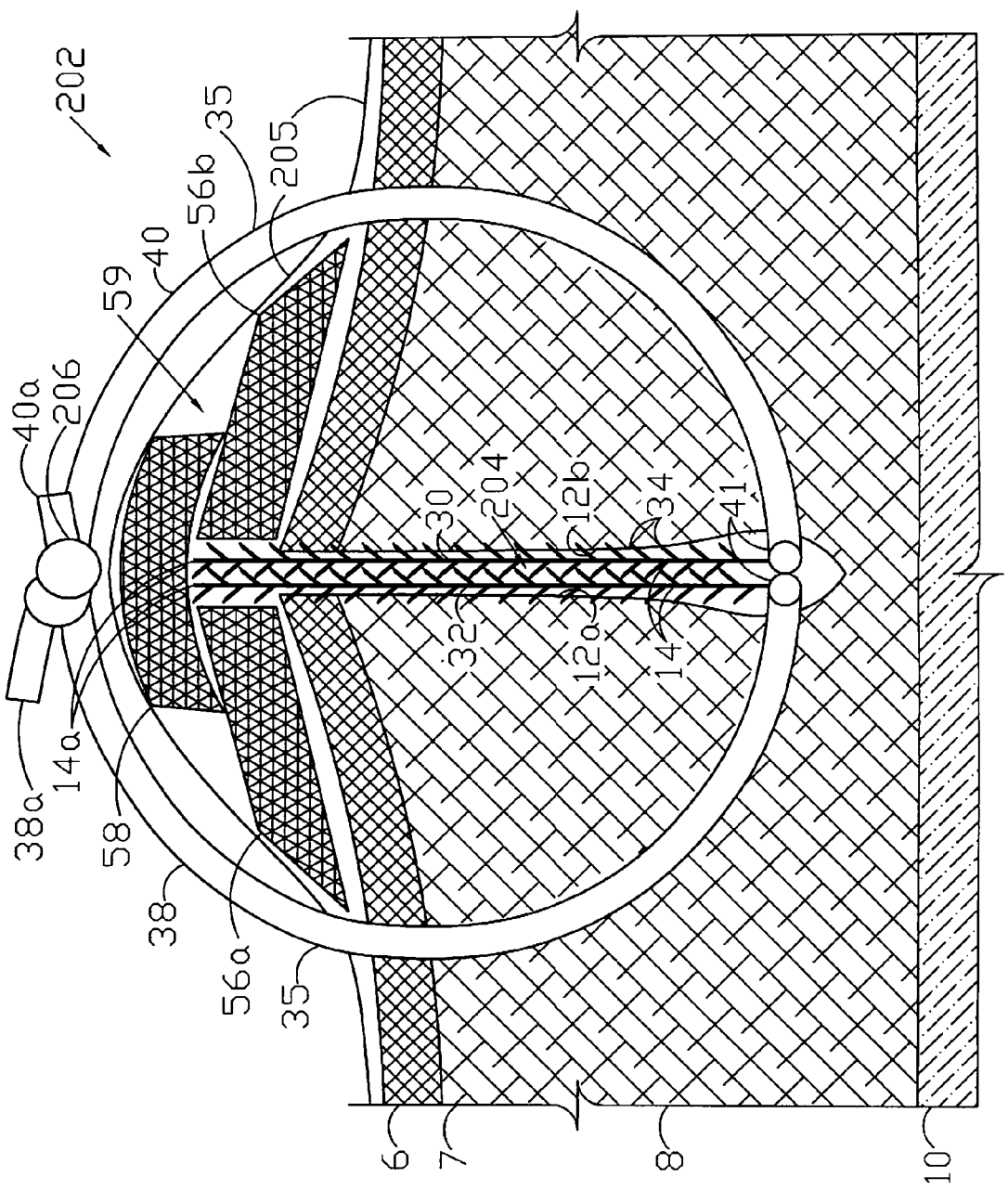
FIG. 8 is a cross-sectional view of a tissue separation closure utilizing tubing for securing the closure screen with a fluid transfer subassembly connected to an upper edge of the closure screen.

FIG. 8 shows a modified embodiment closure system 202 with a pair of screens 14 positioned generally end-to-end in a separation 204. A transfer element subassembly 59 is placed over the separation 204 and a membrane drape 205 is placed thereover. The tube 35 is passed through tissue on either side of the separation 204 (e.g., using the procedure and the tubing placement tool 120 described above) and exits the dermis 6 on either side of the transfer element subassembly 59. The tube 35 lengths are knotted at 206. The tube 35 lengths thus function as sutures or retainers for securing the closure system 202 in the separation 204. The tube ends 38a or 40a can be utilized for this purpose, thus leaving the other tubing ends available for fluid communication with one or more of the input/output subsystems 18 described above.

The tube 35 can be secured by suitable fasteners, such as clips and the like, located above the dermis 6. Moreover, the screens 14 can be overlapped, abutted, spaced slightly and otherwise configured and positioned as necessary for particular tissue separations. Still further, the screens 14 are adapted to be trimmed as necessary.

FIG. 9 shows a modified embodiment tubing/suture subassembly 220 with a needle 222 including a sharpened, distal end 224 and a proximate end 226 with multiple, annular ridges 226a. A length of flexible tubing 228 combines the functions of screen perimeter member and suture. The flexible tubing 228 terminates at an end 228a adapted for releasably mounting on the needle proximate end 226, whereat it is retained in place by the ridges 226a. The tubing 228 is optionally connected to the screen 14 as described above and can include perforations 228b for fluid drainage and/or irrigation in conjunction with input/output subsystems 18, also as described above. The tubing/suture subassembly 220 is adapted for securing the screen 14 in place and for closing the separation 4 by passing the tubing 228 through adjacent tissue. The tubing/suture subassembly 220 and the screen 14 can be prepackaged and presterilized for closing and treating separations, which can include wounds and incisions.

Figure 10:
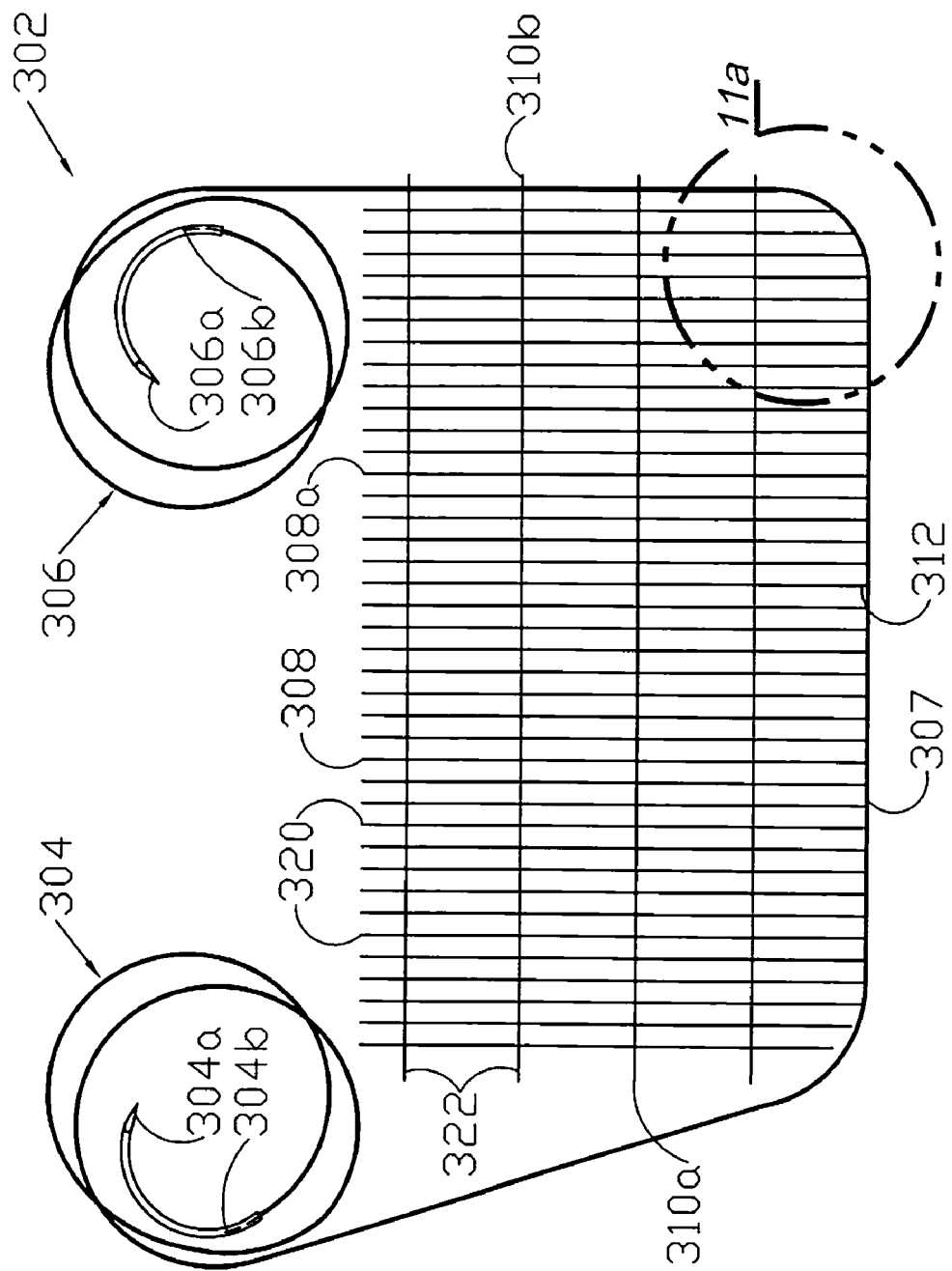
FIG. 10 is a side elevational view of a closure screen comprising an alternative embodiment of the present invention, with a perimeter suture.
Figure 11B:
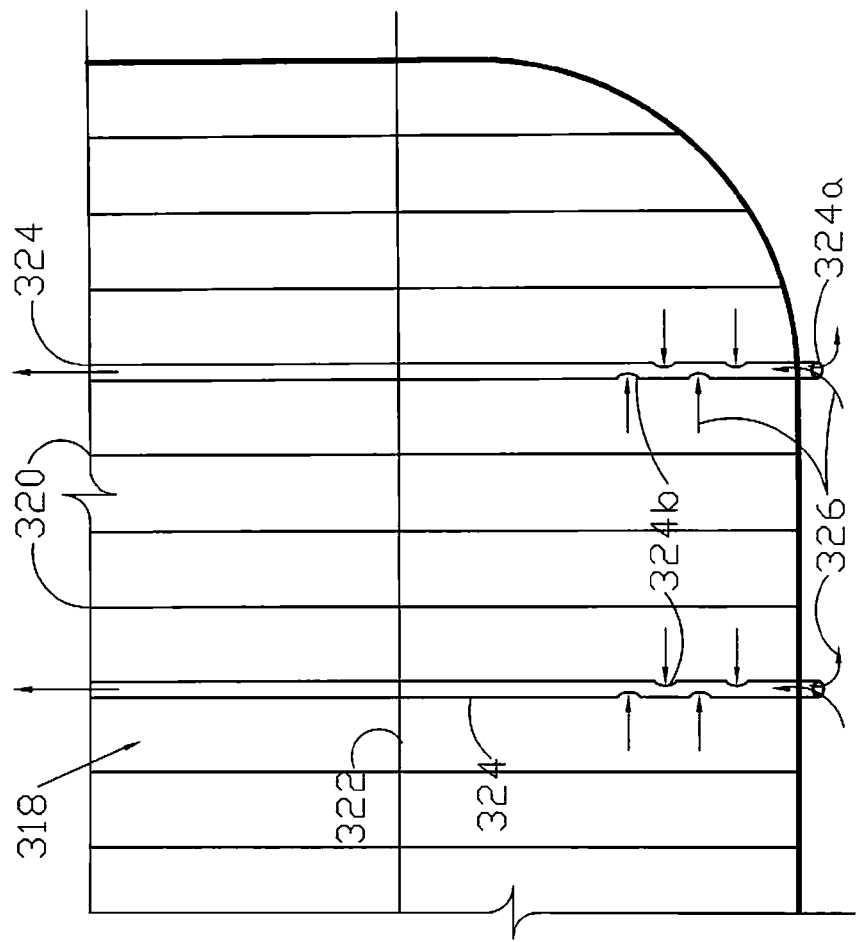
FIG. 11b is an enlarged, fragmentary, side elevational view thereof, showing modified vertical risers.
Figure 11A:
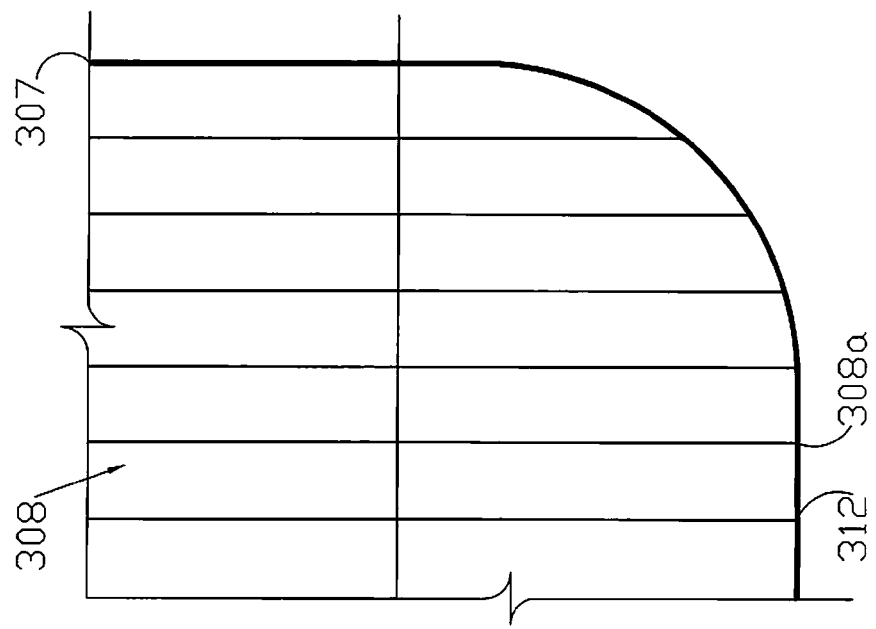
FIG. 11a is an enlarged, fragmentary, side elevational view thereof, taken generally within circle 11a in FIG. 10.

FIGS. 10, 11a and 11b show modified embodiment closure screen systems 302 with first and second suture subassemblies 304, 306 comprising the screen perimeter member. The suture subassemblies 304, 306 include respective curved needles 304a, 306a which are swaged or adhesively connected to opposite ends 304b, 306b of a common length of suture thread 307. The suture thread 307 can be absorbable or nonabsorbable. As shown in FIG. 10, the screen closure system 302 can be preassembled with the suture thread length 307 releasably secured to the perimeter 308a of a screen 308. Prior to installation of the screen 308, the suture 307 can be disconnected or severed therefrom, either partly or completely. For example, the suture 307 can be separated along the screen ends 310a, 310b respectively, thereby leaving the suture thread lengths secured only along a screen lower margin 312.

In operation, the suture subassemblies 304, 306 facilitate installation of the suture/screen closure system 302, thereby providing a preassembled device which incorporates the necessary components for securing same in a separation 4. For example, the screen 308 can be secured at the bottom alone by passing the suture subassemblies 304, 306 through tissue portions located at the bottom of the separation 4. Alternatively, the suture subassemblies 304, 306 can be passed through the adjacent tissue and exit the surface of the dermis 6, whereby the suture subassemblies 304, 306 can be used for closing the separation 4 at the dermis 6. Barbed strands 320 can interact with the tissue portions 12a,b as described above, whereby the screen 308 provides a relatively secure mechanical connection between the separated tissue portions 12a,b. The suture subassemblies 304, 306 can be utilized for various purposes in the separation 4, including attachment and tacking of the dermis 6, the deep dermal layer 7, the subcutaneous layer 8 and the fascia 10. Still further, all or part of the suture subassemblies 304, 306 can be removed, and additional suture subassemblies can be mounted on or sutured to the screen 308.

FIG. 11a shows the screen 308 attached to the suture thread 307. FIG. 11b shows an alternative construction screen 318 with hollow tubular vertical risers 324 located between adjacent, respective vertical strands 320, all connected by the spacers 322 and adapted for communicating fluid with the separation 4 through the open riser ends 324a and the perforations 324b, as indicated by the fluid flow arrows 326. All or part of the screen/suture system 302 can comprise absorbable material.

Figure 13B:
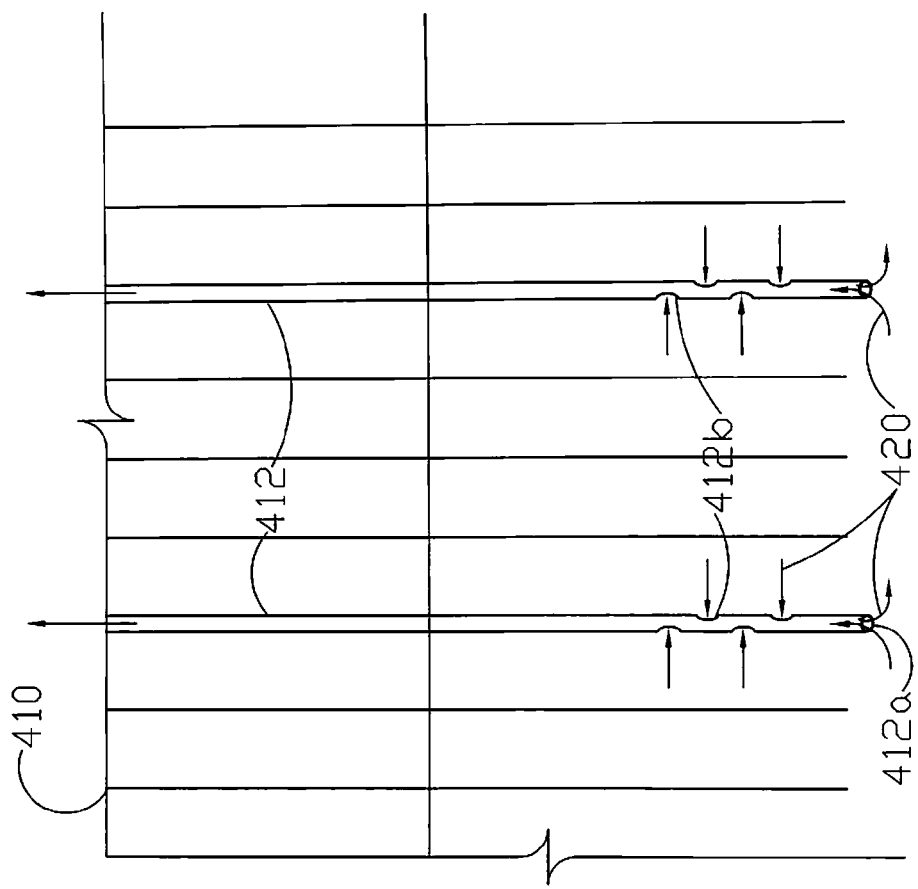
FIG. 13b is an enlarged, fragmentary, side elevational view thereof, showing modified vertical risers.
Figure 13A:
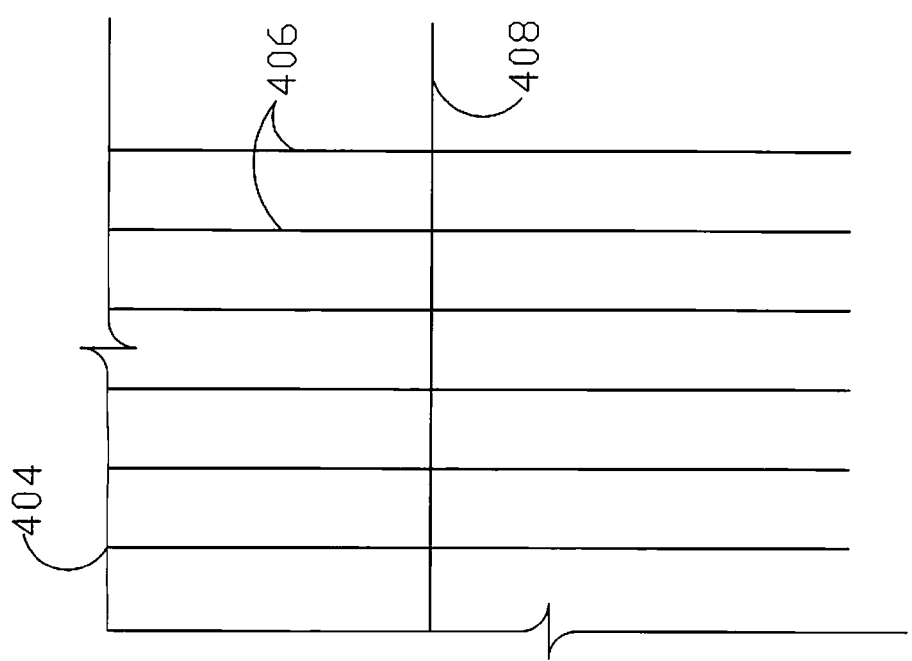
FIG. 13a is an enlarged, fragmentary, side elevational view thereof, taken generally within circle 13a in FIG. 12.

FIGS. 12, 13a and 13b show a modified embodiment screen-only closure screen system 402 and application methodology. A screen or mesh 404, similar to the screen 14 with barbed strands 30 described above, is placed in a separation 4 against the first tissue portion 12a. The second tissue portion 12b is then placed against the screen 404 whereby the separation 4 is closed and can be secured by the mechanical action of the screen 404. The screen 404 can be supplemented with sutures, drainage tubing, I/O devices, and other auxiliary components for purposes of closing the wound edges 12, draining the inside of the tissue separation 4, fighting infection, pain management and all other functionalities associated with the present invention, as discussed elsewhere herein. For example, the screen 404 can be secured with sutures at the subcutaneous level 8. Various fluid interconnecting devices can be utilized as necessary, and can be designed for removal after they serve their initial purpose. External drainage can also be achieved at the dermis level 6 utilizing transfer element subassemblies, such as the example designated 59 and described above (FIG. 7d). Moreover, drainage and irrigation tubing can be installed within the wound 4 alongside or adjacent to the screen 404. It will be appreciated that a screen-only version of the invention can comprise various suitable biocompatible absorbable and non-absorbable materials, including the materials disclosed above.

FIG. 13a is an enlarged view of the screen 404 and particularly shows barbed strands 406 and horizontal spacers 408, which are connected together in a grid pattern forming the screen 404. FIG. 13b shows an alternative embodiment with a modified screen 410 including vertical risers 412 comprising hollow tubing, which are connected to and spaced by horizontal spacers 408. Fluid flows into and out of the vertical risers 412 through open riser ends 412a and perforations 412b, as indicated by the fluid flow arrows 420.

Figure 14A:
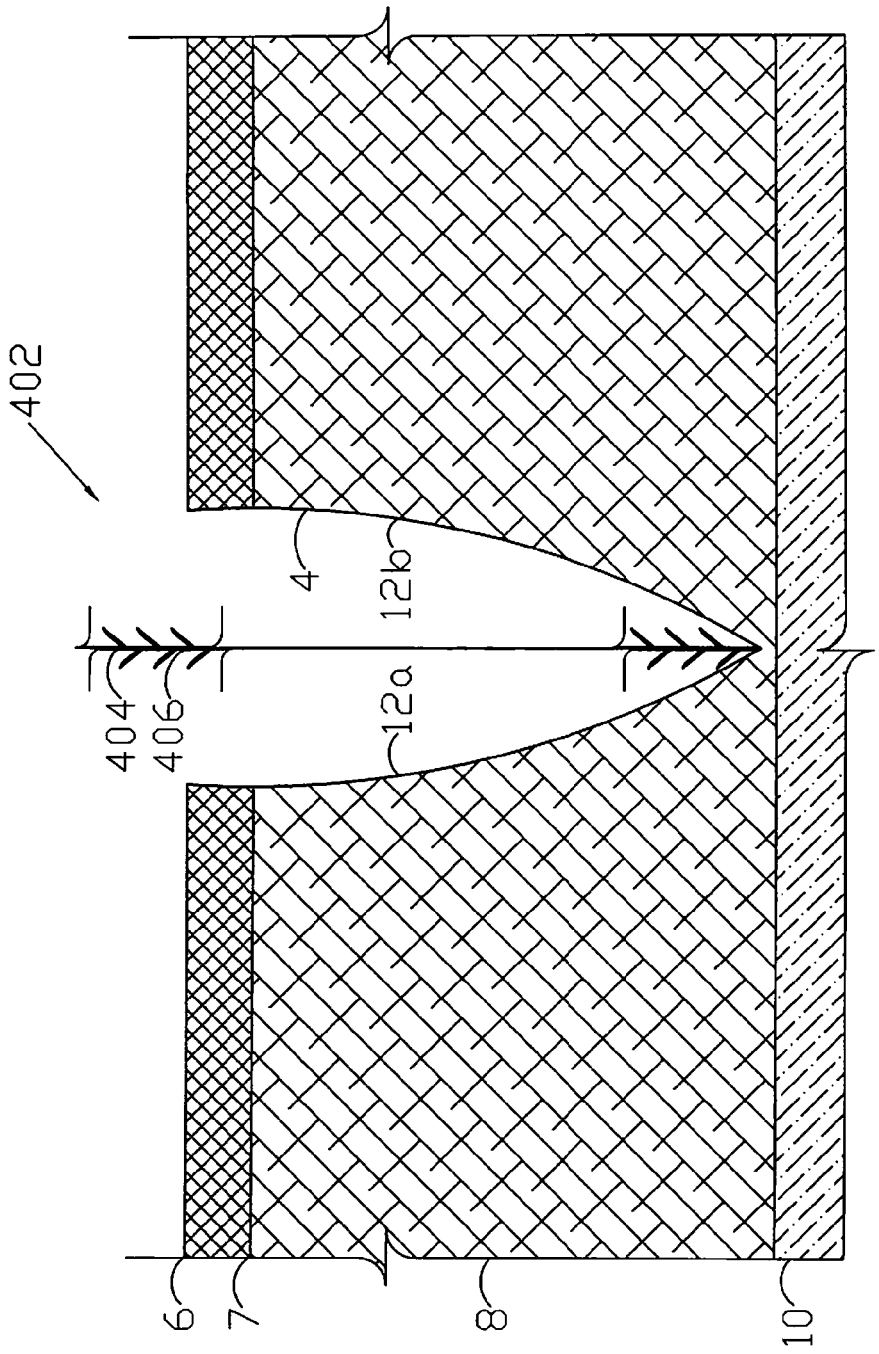
Figure 14C:
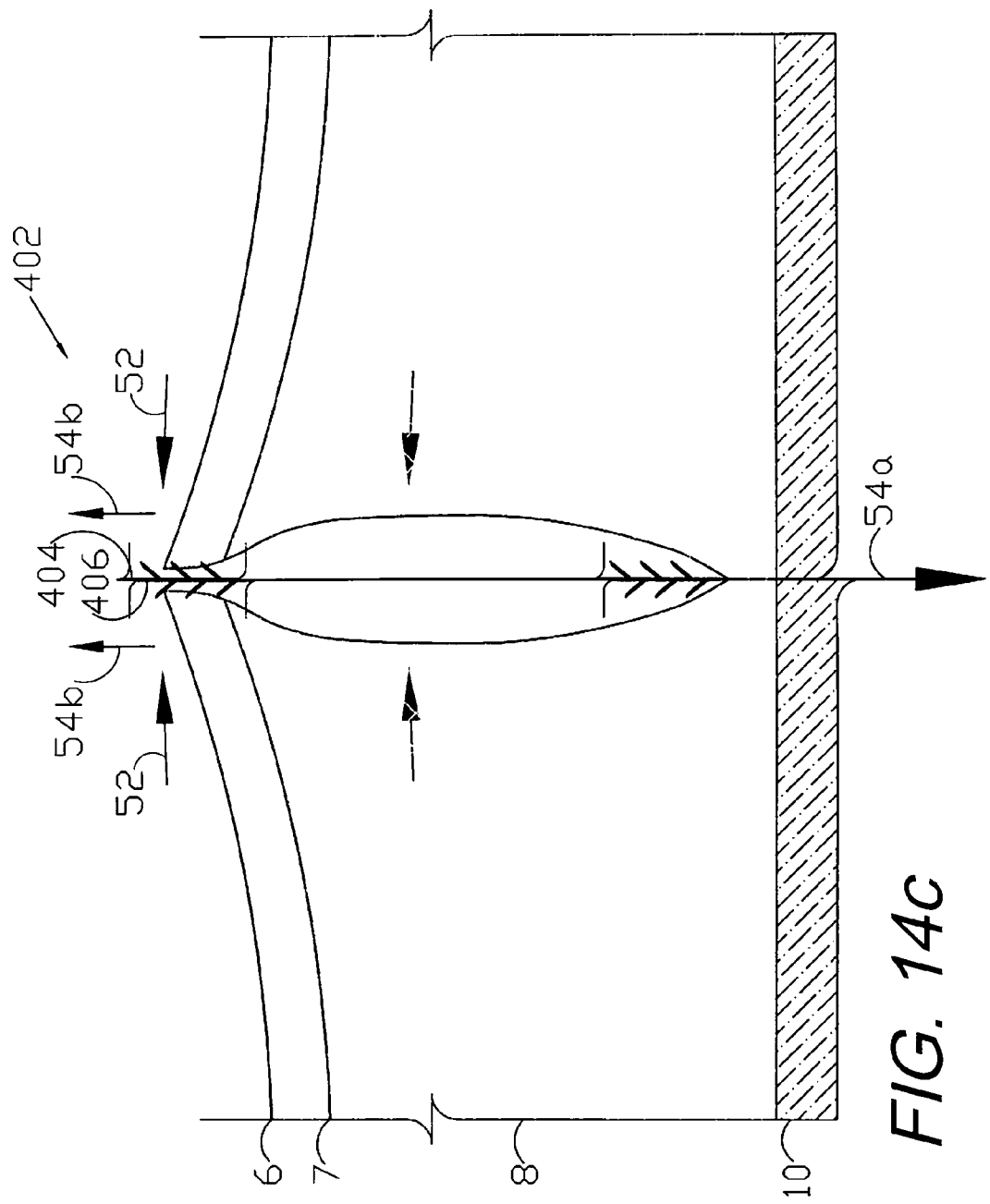
Figure 14D:
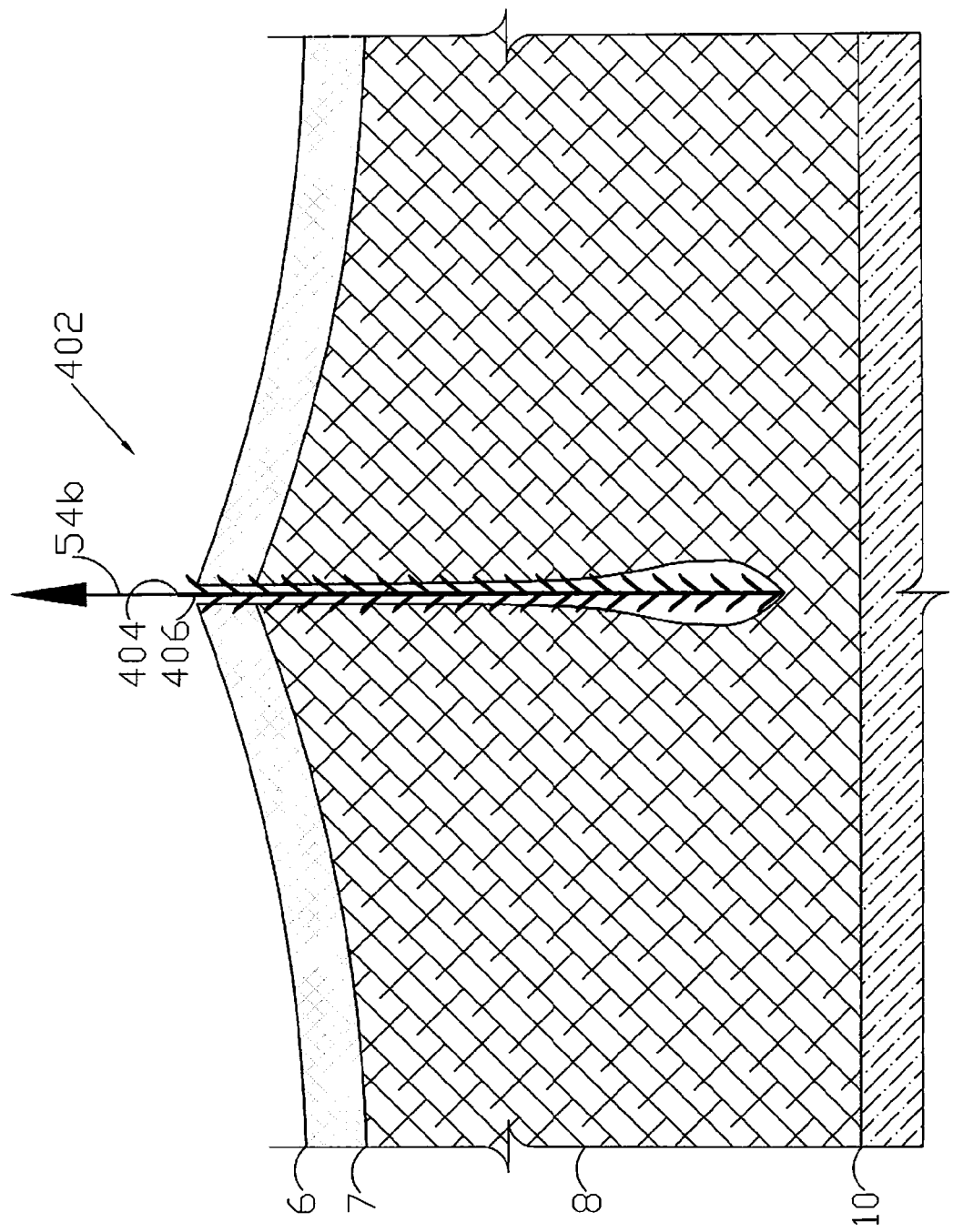
Figure 14G:
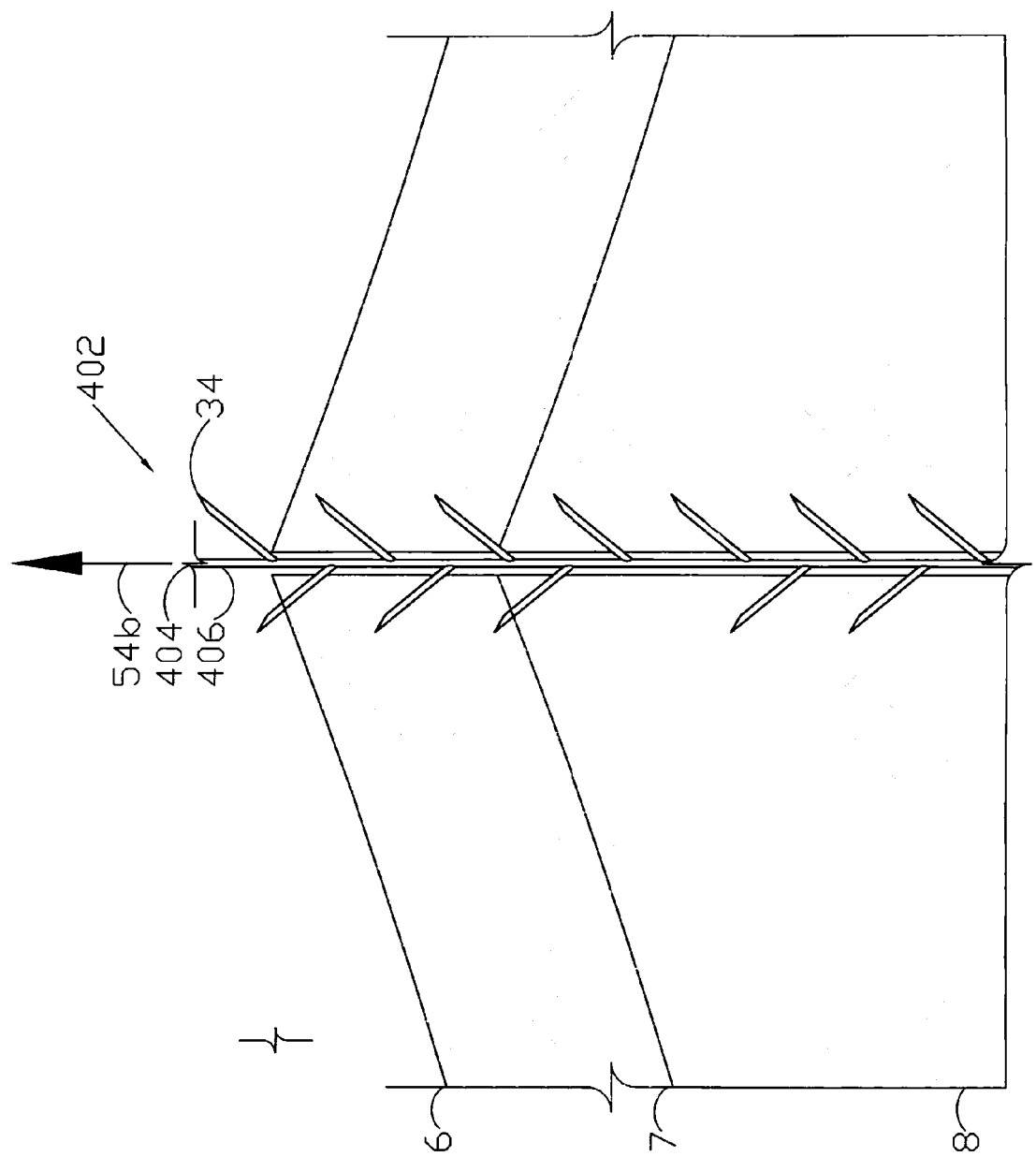

FIGS. 14a-g show the screen 404 installed in a tissue separation 4 and closing same, utilizing the methodology of the present invention. The methodology shown in FIGS. 14a-g is similar to the methodology shown in FIGS. 5a-e and 6a,b. FIG. 14c shows a downward/inward force arrow 54a indicating a direction in which the screen 404 is pushed or guided into the separation.

FIGS. 15a,b and 16a,b show a modified vertical riser 502 comprising bundled tubes 504 secured together at spaced intervals by connectors 506. The normal movement of the patient tends to alternately compress and expand the vertical risers 502, thus providing a "pumping" action for transferring fluid from the wound 4, as indicated by the fluid flow arrows 510. FIGS. 15a,b show a riser 502 in an extended configuration. Compressing the screen 14 longitudinally (i.e., end-to-end) compresses the bundled risers 504 to the configuration shown in FIGS. 16a,b, whereby fluid is drawn into the interstitial space 508 and pumped therefrom when the risers 502 extend.

FIG. 17 shows yet another configuration of a vertical riser 602 with bundled tubes 604, which are closely bunched and define passages 606 for conveying fluid. Such fluid conveyance can be enhanced by a pumping action associated with normal patient movements. Barbs 608 project outwardly from the tubes 604. It will be appreciated that various other bundled tube configurations, such as twisted, braided, etc., can be utilized.

Figure 18:
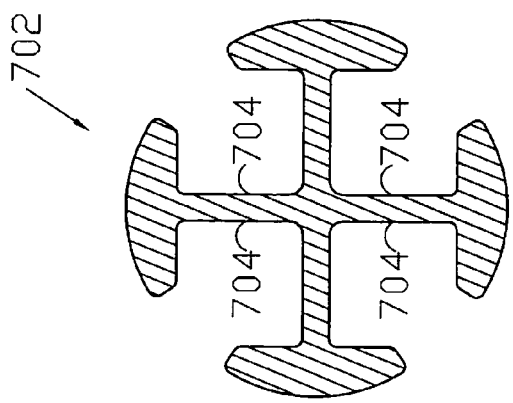
FIG. 18 is a cross-sectional view of a modified vertical riser or perimeter element, comprising a fluted tube.

FIG. 18 shows yet another vertical riser/perimeter member 702 alternative embodiment configuration. The member 702 has a configuration which is commonly referred to as a "fluted" drain and includes longitudinally-extending passages 704. This configuration can substitute for the perimeter members described above and can function to communicate fluid to and from the wound 4 with the input/output subsystem 18.

As additional alternative embodiment configurations for the vertical risers, they can comprise either barbed monofilament strands, similar to strand 30 shown in FIG. 3, or unbarbed monofilament strands. Such monofilament vertical risers can function as passive drains with fluid flowing alongside same. They can extend above the dermis 6 and abut or connect to transfer elements formed in various configurations with suitable absorbent materials. Examples include gauze dressings and transfer element subassemblies, such as 59 shown in FIG. 7d.

Figure 19:
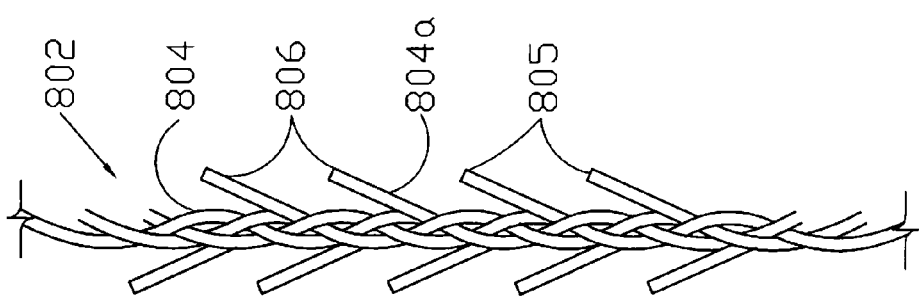
FIG. 19 is an enlarged, fragmentary, side elevational view of a modified barbed strand configuration.

FIG. 19 shows an alternative embodiment strand 802 constructed by twisting and braiding multiple, individual filaments 804. Barbs 805 are formed by respective individual filaments 804a, which terminate at blunt ends 806. The barbs 805 project generally outwardly from the strand 802 and form acute angles with respect to its longitudinal axis. They are adapted for penetrating tissue within a separation 4, as described above. In use, the barbs 805 would normally be oriented in directions generally pointing outwardly from the patient and the tissue separation 4.

Figure 20:
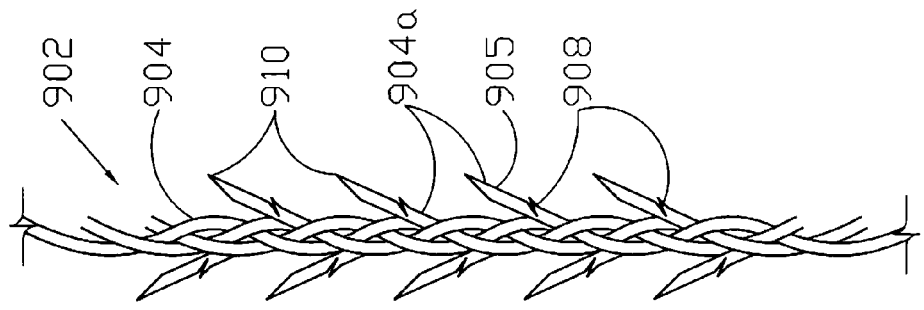
FIG. 20 is an enlarged, fragmentary, side elevational view of another modified barbed strand configuration.

FIG. 20 shows another alternative embodiment strand 902 comprising multiple twisted and braided filaments 904. Barbs 905 are formed from individual filaments 904a and have notches 908 and pointed ends 910. The notches 908 and the ends 910 are configured to allow the barbs 905 to easily extract from the separation edge tissues, whereby the screen is adapted for sliding along the separation edges in order to achieve the proper position.

FIG. 21 shows a further modified screen 1002 with barbs 1004 formed by looping individual filaments 1006 and cutting same at cut locations 1010 spaced inwardly from respective apexes 1008 of the filament loops. In operation, the barbs 1004 slightly penetrate the tissue and are imbedded therein. It will be appreciated that the filaments 1006 are relatively thin in diameter, similar to microfibers, whereby patient comfort is optimized.

FIG. 22 shows yet another modified screen 1102 with barbs 1104 formed by looping individual filaments 1106 and cutting same at locations 1110 spaced inwardly from respective apexes 1108 of the filament loops whereby respective hooks 1112 are formed. The hooks 1112 operate in a manner similar to hook-and-loop fasteners, with the adjacent tissue forming the loop parts of the connections. In operation, the hooks 1112 slightly penetrate the tissue and are imbedded therein. The configurations of the hooks 1112 tend to retain them in the tissue adjacent to the separation 4 whereby the separated first and second tissue portions 12a,b can be closed.

Figure 23:
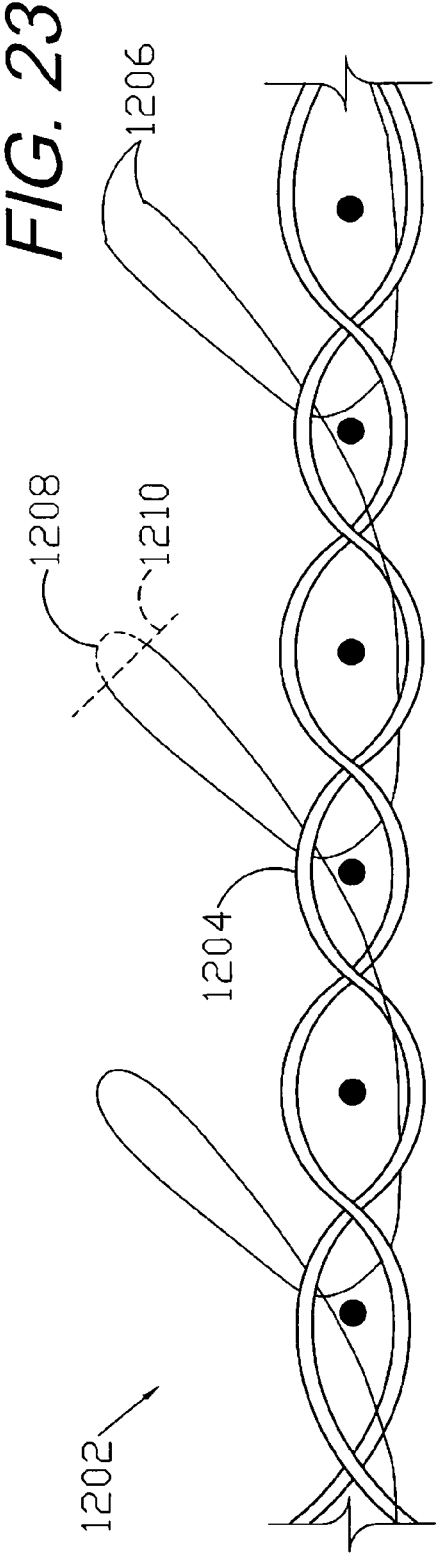
FIG. 23 is an enlarged, cross-sectional view of a closure screen comprising yet another alternative embodiment of the present invention, with barbs formed by cutting off the ends of looped filaments, which are laid over in a common direction or orientation.

FIG. 23 shows a screen 1202 with a configuration similar to the screen 1002 discussed above, with additional fiber elements or filaments 1204. The additional filaments 1204 tend to lay the filament barbs 1206 over whereby the screen 1202 can be directionally oriented within the wound separation 4 and operate in a manner similar to the screen 14 described above. The barbs 1206 are formed by cutting the apexes 1208 at cut locations 1210.

Figure 24:
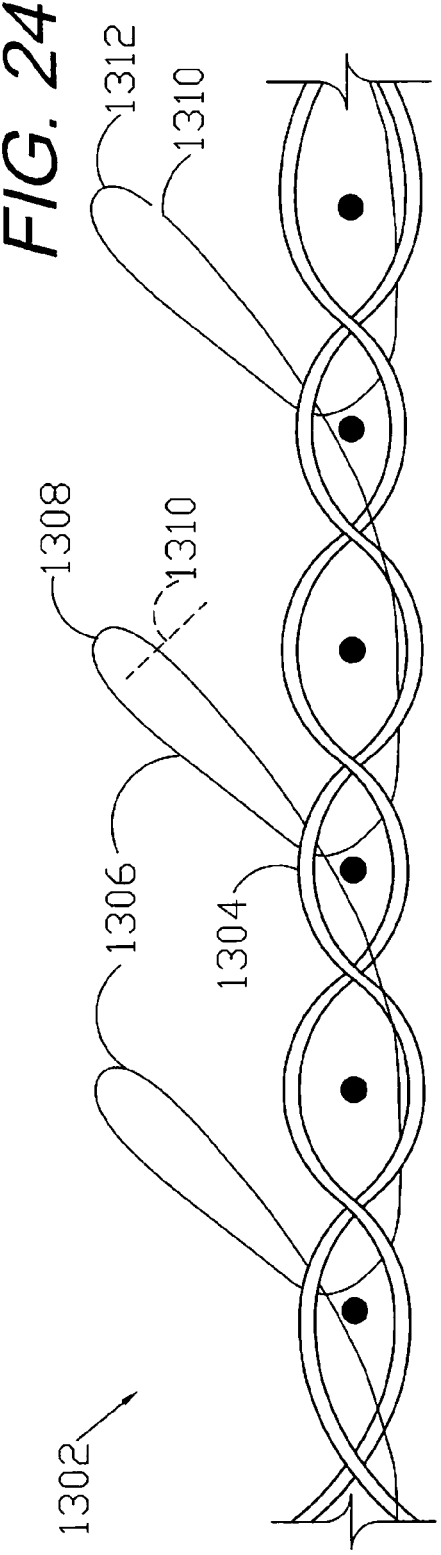
FIG. 24 is an enlarged, cross-sectional view of a closure screen comprising a further alternative embodiment of the present invention, with barbs forming hooks and constructed by cutting looped filaments, which are laid over in a common direction or orientation.

Similarly, FIG. 24 shows a screen 1302 with additional filaments 1304, which engage the filament loops 1306 and orient same in a direction towards the right as shown in FIG. 24. The slanted orientations of the filament loops 1306 facilitate setting same in the tissue portions 12a,b adjacent to the separation 4 by tugging outwardly on the screen 1302. Repositioning the screen 1302 is also possible, as described above. The filament loops 1306 can be cut at cut locations 1310, which are spaced inwardly from filament loop apexes 1308 whereby hooks 1312 are formed.

It will be appreciated that FIGS. 21-24 disclose screens with barbs and hooks extending from one face thereof. The present invention also includes screens with barbs and hooks extending from both faces.

It is to be understood that while certain forms of the present invention have been illustrated and described herein, it is not to be limited to the specific forms or arrangement of parts described and shown.

Having thus described the invention, what is claimed as new and desired to be secured by Letters Patent is:

1. A device for closing a separation of first and second portions of body tissue, which device comprises:
    a closure member with a perimeter and first and second faces;
    said closure member being adapted for positioning at least partly within said separation and including a protruding upper margin adapted to protrude above a skin surface at said separation;
    first and second retainers associated with said first and second faces respectively and adapted to retain same in contact with said first and second body tissue portions respectively;
    a perimeter tube attached to said closure member perimeter and having first and second tube ends;
    first and second input/output devices connected to said perimeter tube first and second ends respectively and adapted for fluidically communicating with said separation;
    a fluid transfer subassembly
    including first and second sponges located on either side of said closure member upper margin and a bridge sponge placed over said first and second sponges above said closure member upper margin, wherein said first and second sponges are adapted to be placed on the skin surface; and
    said fluid transfer subassembly being connected to a vacuum source.

2. A device for closing a separation of first and second portions of body tissue, which device comprises:
    a closure member with a perimeter and first and second faces;
    said closure member being adapted for positioning at least partly within said separation;
    first and second retainers associated with said first and second faces respectively and adapted to retain same in contact with said first and second body tissue portions respectively;
    a perimeter tube attached to said closure member perimeter and having first and second tube ends;
    first and second input/output devices connected to said perimeter tube first and second ends respectively and adapted for fluidically communicating with said separation;
    said closure screen includes multiple hollow risers, which fluidly communicate with said perimeter tube;
    said risers comprising multiple members joined together in bundles and forming fluid passages therebetween;
    said risers are joined together at spaced intervals;
    said risers are adapted for receiving fluid and pumping same in response to patient movements; and
    wherein said perimeter member and said risers are fluidically interconnected to form a fluid distribution manifold at said screen perimeter and extending across an interior of said screen.

3. The device according to claim 2 wherein said risers include perforations.

4. A method of closing separated first and second portions of body tissue at a separation, which method comprises the steps of:
    providing a closure member with a perimeter and first and second faces;
    said closure member being adapted for positioning at least partly within said separation and including a protruding upper margin protruding above a skin surface at said separation;
    providing first and second retainers associated with said first and second faces respectively and retaining same in contact with said first and second body tissue portions respectively;
    providing a perimeter tube attached to said closure member perimeter and having first and second tube ends;
    connecting first and second input/output devices to said perimeter tube first and second ends respectively and fluidically communicating with said separation;
    providing a fluid transfer subassembly including first and second sponges and a bridge sponge;
    extending said closure screen above a skin surface adjacent to said tissue separation;
    placing said first and second sponges located on either side of said closure member upper margin on the skin surface;
    placing said bridge sponge over said first and second sponges above said closure member upper margin; and
    fluidically connecting said fluid transfer subassembly to said closure member and a fluid transfer system;
    transferring fluid from said closure member to said fluid transfer system via said fluid transfer element;
    drawing a vacuum through said closure member and through said tubular fluid transfer element; and
    drawing fluid from said closure member and said fluid transfer element with said fluid transfer system.

5. A method of closing separated first and second portions of body tissue at a separation, which method comprises the steps of:
- providing a closure member with a perimeter and first and second faces;
- providing barbs projecting outwardly from said first and second closure member faces;
- positioning said closure member at least partly in said separation;
- penetrating tissue at said separation with said barbs to secure said first and second closure member faces to said first and second portions of said tissue at said separation;
- closing said separated tissue portions;
- providing said closure member with a screen including proximate and distal margins and multiple, flexible strands extending generally between said margins;
- providing each said strand with multiple barbs projecting outwardly therefrom;
- providing a perimeter member with first and second perimeter member ends;
- attaching said perimeter member to said closure screen perimeter;
- positioning said perimeter member in said tissue separation with said first end extending outwardly from said tissue separation;
- providing said perimeter member with a tubular configuration open at said first end;
- transferring fluid through said perimeter member first end to said tissue separation;
- providing said screen with multiple risers extending generally between proximate and distal margins thereof;
- providing each said riser with a tubular configuration and orifices;
- transferring fluid between said risers and said tissue separation area through said orifices;
- forming said risers with multiple members joined together and forming fluid passages therebetween;
- joining said risers together in bundles at spaced intervals;
- receiving fluid with said risers and pumping same in response to patient movements; and
- fluidically interconnecting said perimeter member and said risers to form a fluid distribution manifold at said screen perimeter and extending across an interior of said screen.

* * * * *

UNITED STATES PATENT AND TRADEMARK OFFICE
CERTIFICATE OF CORRECTION

PATENT NO.        : 8,123,781 B2
APPLICATION NO.   : 12/130516
DATED             : February 28, 2012
INVENTOR(S)       : David S Zamierowski It is certified that error appears in the above-identified patent and that said Letters Patent is hereby corrected as shown below:

In Column 1, Lines 7-17 please replace:

"This application is a continuation and claims priority in application Ser. No. 10/224,852, filed Aug. 21, 2002, now U.S. Pat. No. 7,381,211, dated Jun. 3, 2008. This application also claims priority in application Ser. No. 11/103,056, filed Apr. 11, 2005, now U.S. Pat. No. 7,410,495, application Ser. No. 11/103,052, filed Apr. 11, 2005, now U.S. Pat. No. 7,413,571, application Ser. No. 11/103,403, filed Apr. 11, 2005, now abandoned, and application Ser. No. 11/103,022, filed Apr. 11, 2005, now U.S. Pat. No. 7,413,570, which are continuations-in-part of the same parent application. All of the foregoing applications are incorporated herein by reference."

with

"This application is a continuation and claims priority in application Ser. No. 10/224,852, filed Aug. 21, 2002, now U.S. Pat. No. 7,381,211, dated Jun. 3, 2008. This application also claims priority in application Ser. No. 11/103,056, filed Apr. 11, 2005, now U.S. Pat. No. 7,410,495, application Ser. No. 11/103,052, filed Apr. 11, 2005, now U.S. Pat. No. 7,413,571, application Ser. No. 11/103,043, filed Apr. 11, 2005, now U.S. Pat. No. 7,351,250, and application Ser. No. 11/103,022, filed Apr. 11, 2005, now U.S. Pat. No. 7,413,570, which are continuations-in-part of the same parent application. All of the foregoing applications are incorporated herein by reference."

Signed and Sealed this
Twenty-ninth Day of May, 2012

David J. Kappos
*Director of the United States Patent and Trademark Office*